US007070926B2

(12) United States Patent
Houtzager et al.

(10) Patent No.: US 7,070,926 B2
(45) Date of Patent: Jul. 4, 2006

(54) CHIMAERIC PHAGES

(75) Inventors: Erwin Houtzager, Amerongen (NL);
Ton Logtenberg, Driebergen (NL);
Cornelis A. de Kruif, El De Bilt (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 09/882,621

(22) Filed: Jun. 15, 2001

(65) Prior Publication Data
US 2003/0054495 A1 Mar. 20, 2003

(51) Int. Cl.
*C12Q 1/68* (2006.01)
(52) U.S. Cl. .................... 435/6; 435/69.1; 435/235.1
(58) Field of Classification Search ............... 435/69.1, 435/456, 457, 489, 173.3, 235.1, 252.3, 320.1, 435/6; 536/23.4; 530/350
See application file for complete search history.

(56) References Cited

U.S. PATENT DOCUMENTS
6,027,930 A * 2/2000 Borrebaeck ............... 435/235.1

FOREIGN PATENT DOCUMENTS
EP     1 266 963 A1    12/2002
WO     WO 02/103012 A1  12/2002

OTHER PUBLICATIONS

Michael F. Moody. Journal of Molecular Biology, 1999, vol. 293, pp. 401-433.*
Balint et al., Antibody engineering by parsimonious mutagenesis, Gene, 1993, pp. 109-118, vol. 137.
Barbas III et al., In vitro evolution of a neutralizing human antibody to human immunodeficiency virus type 1 to enhance affinity and broaden strain cross-reactivity, Proc. Natl. Acad. Sci., Apr. 1994, pp. 3809-3813, vol. 91, USA.
Bass et al., Hormone Phage: An Enrichment Method for Variant Proteins With Altered Binding Properties, Proteins: Structure, Function, and Genetics, 1990, pp. 309-314, vol. 8.
Beekwilder et al., A phagemid vector using the *E. coli* phage shock promoter facilitates phage display of toxic proteins, Gene, 1999, pp. 23-31, vol. 228.
Berek et al., Mutation Drift and Repertoire Shift in the Maturation of the Immune Response, Immunological Reviews, 1987, pp. 23-41, No. 96.
Burton et al., Human Antibodies from Combinatorial Libraries, Advances in Immunology, pp. 191-280, vol. 57.
Chatellier et al., Interdomain interactions within the gene 3 protein of filamentous phage, FEBS Letters, 1999, pp. 371-374, vol. 463.
Crissman et al., Gene-III Protein of Filamentous Phages: Evidence for a Carboxyl-Terminal Domain with a Role in Morphogenesis, Virology, 1984, pp. 445-455, vol. 132.

Cwirla et al., Peptides on phage: A vast library of peptides for identifying ligands, Proc. Natl. Acad. Sci., Aug. 1990, pp. 6378-6382, vol. 87.
De Kruif et al., Selection and Application of Human Single Chain Fv Antibody Fragments from a Semi-synthetic Phage Antibody Display Library with Designed CDR3 Regions, J. Mol. Biol., 1995, pp. 97-105, vol. 248.
De Kruif et al., Rapid selection of cell subpopulation-specific human monoclonal antibodies from a synthetic phage antibody library, Proc. Natl. Acad. Sci., Apr. 1995, pp. 3938-3942, vol. 92, USA.
Deng et al., Interaction of the Globular Domains of pIII Protein of Filamentous Bacteriophage fd with the F-Pilus of *Escherichia coli*, Virology, 1999, pp. 271-277, vol. 253.
Devlin et al., Random Peptide Libraries: A Source of Specific Protein Binding Molecules, Science, Jul. 27, 1990, pp. 404-406, vol. 249.
Duenas et al., Clonal Selection and Amplification of Phage Displayed Antibodies by Linking Antigen Recognition and Phage Replication, Bio/Technology, Oct. 1994, pp. 999-1002, vol. 12.
Duenas et al., Novel helper phage design: intergenic region affects the assembly of bacteriophages and the size of antibody libraries, FEMS Microbiology Letters, 1995, pp. 317-322, vol. 125.
Felici et al., Mimicking of discontinuous epitopes by phage-displayed peptides, II. Selection of clones recognized by a protective monoclonal antibody against the *Bordetella pertussis* toxin from phage peptide libraries, Gene, 1993, pp. 21-27, vol. 128.

(Continued)

*Primary Examiner*—James Ketter
(74) *Attorney, Agent, or Firm*—TraskBritt

(57) ABSTRACT

A chimeric phage having a coat comprising a mixture of proteins. The mixture of proteins includes a fusion protein wherein a protein is fused to a functional form of a phage coat protein, and a mutant form of the phage coat protein characterized in that a phage having no wild type phage coat protein from which the mutant form is derived but having a coat comprising the mutant form and no copies of the functional form is less infectious than a phage comprising no wild type phage coat protein from which the mutant form is derived and having a coat comprising the mutant form and at least one copy of the functional form. Also, the associated phage collection comprising the chimaeric phage or an infectious phage containing at least one copy of a mutant form of a phage coat protein wherein the mutant form has lost the ability to mediate infection of a natural host by the infectious phage. Also a method for producing a phage particle. Also, a helper phage having a nucleic acid encoding phage proteins or functional equivalents for the assembly of the helper phage.

14 Claims, 10 Drawing Sheets

OTHER PUBLICATIONS

Hawkins et al., Selection of Phage Antibodies by Binding Affinity, Mimicking Affinity Maturation, J. Mol. Biol., 1992, pp. 889-896, vol. 226.

Holliger et al., A conserved infection pathway for filamentous bacteriophages is suggested by the structure of the membrane penetration domain of the minor coat protein g3p from phage fd, Structure, 1997, pp. 265-275, vol. 5, No. 2.

Hoogenboom et al., Designing and optimizing library selection strategies for generating high-affinity antibodies, TIB Tech, Feb. 1997, pp. 62-70, vol. 15.

Krebber et al., Co-selection of cognate antibody—antigen pairs by selectively-infective phages, FEBS Letters, 1995, pp. 227-231, vol. 377.

Krebber et al., Selectively-infective Phage (SIP): A Mechanistic Dissection of a Novel in vivo Selection for Protein-ligand Interactions, J. Mol. Biol. 1997, pp. 607-618, vol. 268.

Kristensen et al., Proteolytic selection for protein folding using filamentous bacteriophages, Folding & Design, pp. 321-328, vol. 3, No. 5.

Low et al., Mimicking Somatic Hypermutation: Affinity Maturation of Antibodies Displayed on Bacteriophage Using a Bacterial Mutator Strain, J. Mol. Biol., 1996, pp. 359-368, vol. 260.

Lubkowski et al., The structural basis of phage display elucidated by the crystal structure of the N-terminal domains of g3p, Nature Structural Biology, Feb. 1998, pp. 140-147, vol. 5, No. 2.

Lubkowski et al., Filamentous phage infection: crystal structure of g3p in complex with its coreceptor, the C-terminal domain of ToIA, Structure, 1999, pp. 711-722, vol. 7, No. 6.

Luzzago et al., Mimicking of discontinuous epitopes by phage-displayed peptides, I. Epitope mapping of human H ferritin using a phage library of constrained peptides, Gene, 1993, pp. 51-57, vol. 128.

Lopez et al., Morphogenesis of Filamentous Bacteriophage f1: Orientation of Extrusion and Production of Polyphage, Virology, 1983, pp. 177-193, vol. 127.

Model et al., The *Escherichia coli* phage-shock-protein (psp) operon, Molecular Microbiology, 1997, pp. 255-261, vol. 24, No. 2.

Nelson et al., Filamentous Phage DNA Cloning Vectors: A Noninfective Mutant with a Nonpolar Deletion in Gene III, Virology, 1981, pp. 338-350, vol. 108.

Nilsson et al., The Phage Infection Process: a Functional Role for the Distal Linker Region of Bacteriophage Protein 3, Journal of Virology, May 2000, pp. 4229-4235, vol. 74.

Pratt et al., Conditional Lethal Mutants of the Small Filamentous Coliphage M13. II. Two Genes for Coat Proteins, Virology, 1969, pp. 42-53, vol. 39.

Rakonjac et al., Filamentous phage infection-mediated gene expression: construction and propagation of the gIII delection mutant helper phage R408d3, Gene, 1997, pp. 99-103, vol. 198.

Rakonjac et al., Roles of pIII in Filamentous Phage Assembly, J. Mol. Biol. 1998, pp. 25-41, vol. 282.

Riechmann et al., The C-Terminal Domain of ToIA Is the Coreceptor of Filamentous Phage Infection of *E. coli*, Cell, Jul. 25, 1997, pp. 351-360, vol. 90.

Rondot et al., A helper phage to improve single-chain antibody presentation in phage display, Nature Biotech, pp. 75-78, vol. 19.

Russel et al., Genetic Analysis of the Filamentous Bacteriophage Packaging Signal and of the Proteins That Interact with It, Journal of Virology, Aug. 1989, pp. 3284-3295, vol. 63, No. 8.

Smith, Filamentous Fusion Phage: Novel Expression Vectors That Display Cloned Antigens on the Virion Surface, Science, Jun. 14, 1985, pp. 1315-1317, vol. 228.

Spada et al., Selectively Infective Phages (SIP), Biol. Chem., Jun. 1997, pp. 445-456, vol. 378.

Vaughan et al., Human antibodies by design, Nature Biotechnology, Jun. 1998, pp. 535-539, vol. 16.

Winter et al., Man-made antibodies, Nature, Jan. 24, 1991, pp. 293-299, vol. 349.

Yang et al., CDR Walking Mutagenesis for the Affinity Maturation of a Potent Human Anti-HIV-I Antibody into the Picomolar Range, J. Mol. Biol., 1995, pp. 392-403.

PCT International Search Report, PCT/NL02/00391, dated Nov. 25, 2002, 3 pages.

Rudert et al., A phage-based system to select multiple protein—protein interactions simultaneously from combinatorial libraries, FEBS Letters, 1998, pp. 135-140, vol. 440.

\* cited by examiner

G3-minus protein

```
GGTTATGCGTGGGCGATGGTTGTTGTCATTGTCGGCGCAACTATCGGTATCAAGCTGTTTAAGAAATTCACCTCG
AAAGCAAGCTGATAAACCGATACAATTAAAGGCTCCTTTTGGAGCCTTTTTTTTTGGAGATTTTCAACAAGCTTC
TGCGTAATAAGGAGTCTTAATCATGCCAGTTCTTTTGGGTATTCCGTTATTATTGCGTTTCCTCGGTTTCCTTCT
GGTAACTTTGTTCGGCTATCTGCTAACTTTTCTTAAAAAGG
```

Figure 6B

D3 domain of g3 Protein

```
TTGACTCCCTGCAAGCCTCAGCGACCGAATATATCGGTTATGCGTGGGCGATGGTTGTTGTCATTGTCGGCGCAA
CTATCGGTATCAAGCTGTTTAAGAAATTCACCTCGAAAGCAAGCTGATAAACCGATACAATTAAAGGCTCCTTTT
GGAGCCTTTTTTTTTGGAGATTTTCAACGTGAAAAAATTATTATTCGCAATTCCTTTAGTTGTTCCTTTCTATTC
TCACTCCGCTAAGCTTTCTGGTTCCGGTGATTTTGATTATGAAAATATGGCAAACGCTAATAAGGGGGCTATGAC
CGAAAATGCCGATGAAAACGCGCTACAGTCTGACGCTAAAGGCAAACTTGATTCTGTCGCTACTGATTACGGTGC
TGCTATCGACGGTTTCATTGGTGACGTTTCCGGCCTTGCTAATGGTAATGGTGCTACTGGTGATTTTGCTGGCTC
TAATTCCCAAATGGCTCAAGTCGGTGACGGTGATAATTCACCTTTAATGAATAATTTCCGTCAATATTTACCTTC
CCTTCCTCAATCGGTTGAATGTCGCCCTTTTGTCTTTCGCGCTGGTAAACCATATGAATTTTCTATTGATTGTGA
CAAAATAAACTTATTCCGTGGTGTCTTTGCGTTTCTTTTATATGTTGCCACCTTTATGTATGTATTTTCGACGTT
TGCTAACATACTGCGTAATAAGGAGTCTTAATCATGCCAGTTCTTTTGGGTATTCCGTTATTATTGCGTTTCCTC
GGTTTCCTTCTGGTAACTTTGTTCGGCTATCTGCTAACTTTTCTTAAAAAGGGCTTCGGTAAGATAGCTATTGCT
ATTTCAT
```

Figure 7B

| A | GCG GCA GCC GCT |
|---|---|
| C | TGC TGT |
| D | GAT GAC |
| E | GAA GAG |
| F | TTT TTC |
| G | GGT GGC |
| H | CAT CAC |
| I | ATT ATC ATG |
| K | AAA |
| L | CTG |
| M | ATG |
| N | AAC AAT |
| P | CCG |
| Q | CAG |
| R | CGT CGC |
| S | AGC TCT |
| T | ACC ACG |
| V | GTG GTT GTC |
| W | TGG |
| Y | TAT TAC |
| STOP | TAA TGA |

Figure 8

CHIMAERIC PHAGES

FIELD OF THE INVENTION

The present invention relates to the fields of molecular biology and immunology. The invention in particular relates to the field of generating helper phages and phage display libraries for the identification of binding molecules.

BACKGROUND OF THE INVENTION

An individual needs to have a dynamic immune system that is able to adapt rapidly to respond adequately to potentially harmful microorganisms and to respond to the exposure of a highly diverse and continuously changing environment. Higher organisms have evolved specialized molecular mechanisms to ensure the implementation of clonally-distributed, highly diverse repertoires of antigen-receptor molecules expressed by cells of the immune system: immunoglobulin (Ig) molecules on B lymphocytes and T cell receptors on T lymphocytes. A primary repertoire of (generally low affinity) Ig receptors is established during B cell differentiation in the bone marrow as a result of rearrangement of germ line-encoded gene segments. Further refinement of Ig receptor specificity and affinity occurs in peripheral lymphoid organs where antigen-stimulated B lymphocytes activate a somatic hypermutation machinery that specifically targets the immunoglobulin variable (V) regions. During this process, B cell clones with mutant Ig receptors of higher affinity for the inciting antigen are stimulated into clonal proliferation and maturation into antibody-secreting plasma cells (reviewed in Berek and Milstein, 1987).

Recombinant DNA technology has been used to mimic many aspects of the processes that govern the generation and selection of natural human antibody repertoires (reviewed in Winter and Milstein, 1991; Vaughan et al. 1998). The construction of large repertoires of antibody fragments (such as Fab fragments or single chain Fv fragments, scFv's) expressed on the surface of filamentous phage particles and the selection of such phages by "panning" on antigens has been developed as a versatile and rapid method to obtain antibodies of desired specificities (reviewed in Burton and Barbas, 1994). A subsequent optimization of the affinity of individual phage antibodies was achieved by creating mutant antibody repertoires of the selected phages and sampled for higher affinity descendents by selection for binding to antigen under more stringent conditions (reviewed in Hoogenboom, 1994).

M13 and M13-derived phages (sometimes also called viruses) are filamentous phages that can selectively infect F-pili bearing (F$^+$) *Escherichia coli* (*E. coli*) cells. The phage genome encodes 11 proteins, while the phage coat itself consists of five of these proteins: gene-3, -6, -7, -8 and -9 (g3, g6, g7, g8 and g9) proteins that are bound to and that protect the (circular) (circular) single stranded DNA (ssDNA) of the viral genome. The life cycle of the virus can be subdivided into different phases. After infection of an *E. coli* by a phage particle, the ssDNA of the virus becomes double stranded due to the action of a number of bacterial enzymes. The double stranded phage genome now serves as a template for the transcription and translation of all 11 genes located on the phage genome. Besides these protein-encoding regions, the phage genome contains an intergenic region: the F1-origin of replication initiation (F1-ORI). The DNA sequence of this F1-ORI can be divided in two separate subregions. One subregion is responsible for the initiation and termination of the synthesis of ssDNA via the so-called "rolling circle mechanism" and the other subregion is responsible for the packaging initiation of the formed circular ssDNA leading to the formation and release of new virus particles.

It has been shown that polypeptides, such as stretches of amino acids, protein parts or even entire proteins can be added by means of molecular genetics to the terminal ends of a number of particle coat proteins, without disturbing the functionality of these proteins in the phage life cycle (Smith, 1985; Cwirla et al. 1990; Devlin et al. 1990; Bass et al. 1990; Felici et al. 1993; Luzzago et al. 1993).

This feature enables investigators to display peptides or proteins on phages, resulting in the generation of peptide- or protein expression phage display libraries. One of the proteins that has been used in the art to fuse with polypeptides for phage display purposes, is the g3 protein (g3p), which is a coat protein that is required for an efficient and effective infectivity and subsequent entry of the viral genome into the *E. coli* cell.

For the production of phages that display polypeptides fused to the g3p coat protein, investigators in the art introduced a plasmid together with the phage genome in *E. coli* cells. This plasmid contains an active promoter upstream of an in-frame fusion between the g3 encoding gene and a gene of interest (X) encoding, for instance, polypeptides, proteins, antibodies or fragments such as Fab fragments or scFv's. The introduction of this plasmid together with the genome of the helper phage in an *E. coli* cell results in the generation of phages that contain on their coat either the wild type g3p from the viral genome, the fusion product g3p-X from the plasmid or a mixture of the two, since one phage particle carries five g3p's on its surface. The process of g3p or g3p-X incorporation is generally random. The presence of an F1-ORI sequence in the g3p-X expression vector (plasmid) misleads the phage synthesis machinery in such a way that two types of circular ssDNA are formed: one is derived from the genome of the phage and the other is derived from the expression vector. During the synthesis of new phages, the machinery is unable to distinguish the difference between these two forms of ssDNA resulting in the synthesis of a mixed population of phages, one part containing the phage genome and one part harboring the vector DNA. Due to these processes, the mixture contains at least some phages in which the phenotypic information on the outside (the g3p-X fusion protein) is conserved within the genotypic information inside the particle (the g3p-X expression vector). An infectious wild type phage and a phage carrying a fusion protein attached to g3p are depicted in FIG. 4. The art teaches that there are several problems that concern the use of these basic set-ups.

The high level of genotypic wild type phages in phage populations grown in bacteria that contain both the phage genome and the expression vector, compelled investigators to design mutant F1-ORI sequences in M13 genomes. Such mutant M13-strains are less effective in incorporating their genome in phage particles during phage assembly, resulting in an increased percentage of phages containing vector sequences when co-expressed. These mutant phages, such as the commercially available strains R408, VCSM13 and M13KO7, are called "helper phages." The genome of these helper phages may contain genes required to assemble new (helper-) phages in *E. coli* and to subsequently infect new F-pili expressing *E. coli*. Both VCSM13 and M13K07 were provided with an origin of replication initiation (ORI) of the P15A type that results in the multiplication of the viral genome in *E. coli*. Moreover, the ORI introduction ensures that after cell division, the old and newly formed E. coli contains at least one copy of the viral genome.

It was suggested and finally proven by several investigators that the introduction of plasmids containing a g3p-scFv fusion product, together with the genome of the helper phages in E. coli cells, results in approximately 99% of newly formed phages that harbor the g3p-scFv fusion protein expression plasmid but, nevertheless, lack the g3p-scFv fusion on its surface (Beekwilder et al. 1999). The absence of g3p-X is a significant disadvantage in the use of display libraries for the identification of specific proteins or peptides, such as scFv's that bind to a target of interest (such as tumor antigens). It implies that in the case of phage display libraries, at least a 100-fold excess of produced phages must be used in an experiment in order to perform a selection with all possible fusion proteins present. The art teaches that this overload of relatively useless phages in an experiment leads to too many false positives. For instance, at least $10^{12}$ phages should be added to a panning experiment in order to have one copy of each possible fusion present in the experiment since such a library contains approximately $10^{10}$ different g3p-scFv fusions (1%). The phages in this approximate 1% express generally only 1 g3p-scFv fusion on their coat together with four normal g3p's (no fusions), while the rest of the helper phages (approximately 99%), express five g3p's and no g3p-scFv fusions. To ensure, theoretically, the presence of 100 copies of each separate fusion protein in a panning experiment, one needs to use approximately $10^{14}$ phages in such an experiment. Persons skilled in the art generally attempt to use an excess of at least 100-fold of each single unique fusion protein to ensure the presence of sufficient numbers of each separate fusion and to prevent losing relevant binders too quickly in first panning rounds. That number of phages ($10^{14}$) is more or less the maximum of phage particles that one milliliter (ml) can hold. The viscosity of such a solution is extremely high and, therefore, relatively useless. Especially when ELISA panning strategies are used (in which the volume of one well is only 200 µl), such libraries cannot be used.

In addition to these problems, it is shown that, depending on the antigen, an average of one in every $10^7$ phages will bind to the antigen due to a-specific binding. Generally, as mentioned, for the addition of $10^{12}$ scFv expressing input phages (1%) to a panning procedure, one has to add approximately $10^{14}$ phages (99% does not express a scFv fragment). It is generally assumed that from these $10^{12}$ phages, approximately $10^4$ particles might be putatively interesting phages. However, the number of calculated background phages that are normally found by using libraries present in the art after one round of panning was approximately $10^6$–$10^7$, while only a few of these phages appear to be relevant binders. This is one of the most significant problems recognized in the art: too many background phages show up as initial binders in the phage mix after the first round of panning, while only a few significant and interesting binders are present in this mix. So, the absolute number of isolated phages after one round of panning is clearly too high ($10^6$–$10^7$). Moreover, in subsequent rounds of panning, non-specific background phages also remain present. In libraries used in the art, most of these non-specific binders will amplify on bacteria to continue appearing in a second round of panning. Therefore, the art teaches that the background level of a-specifically binding phages and the total number of phages per ml in these types of libraries is unacceptably high and remains high during subsequent rounds of panning.

A possibility that was suggested by investigators in the art as a solution to the problem of obtaining too many background phages that lack a g3p-X fusion, was to remove the g3p-encoding gene entirely from the helper phage genome. In principle, this system ensures that during phage synthesis in an E. coli cell (that received the g3-less phage genome and a g3p-X fusion protein expression vector), only g3p-X proteins are incorporated in the newly formed phage coat. By doing so, each synthesized phage will express five copies of the g3p-X fusion product and hardly any phages are synthesized that express the g3p alone or that express less than five g3p-X fusions. R408-d3 and M13αD3 are two examples of g3-minus helper phages (Dueòas and Borrebaeck, 1995; Rakonjac et al. 1997). Because the genome of these phages in not capable of supporting g3p synthesis, phage particles that carry less than five g3p-X fusion proteins can hardly be formed or, if formed, are found to be non-infectious due to instability, since the art teaches that five g3p's are necessary to ensure a stable phage particle.

To produce helper phages that do not contain the g3 gene but that are, nevertheless, infectious, that can be used to generate libraries of phages that carry five g3p-X fusion proteins, and that lack phages with less than five g3p-X fusions, it was recognized in the art that an external source for g3p was required. Such a source can be a vector without F1-ORI but that, nevertheless, contains an active promoter upstream of the full open reading frame (ORF) of g3. One major problem that is recognized by persons skilled in the art is that after the generation step of producing newly formed helper phages lacking a g3 gene, the yield is dramatically low. In fact, the yield of all described systems is below $10^{10}$ phages per liter, meaning that for a library of $10^{10}$ individual clones, at least 100 liters of helper phage culture is necessary (NB: the helper phages need to be purified) in order to grow the library once. Thus, the art teaches that phage libraries generated with such low titers of helper phages are not useful for phage display purposes and that, therefore, these libraries cannot be used for panning experiments.

Phages that express deleted g3p's fused to heterologous proteins have also been generated. For the construction of most conventional Fab libraries and some scFv phage display libraries, the D1 domain, and parts of the D2 domain, were removed to ensure a shorter fusion protein, which was considered in the art as a product that could be translated easier than a full length g3p linked to a full length Fab fragment. The shorter g3p part would not prevent the generation of a viable and useful helper phage. Of course, such phages still depend on full length g3p's that are present on their surface next to the deleted g3p fusion with the Fab fragment for functional infectivity of E. coli cells. Also, phages that express deleted g3p's fused to ligand-binding proteins have been generated that depend on their infectious abilities on antigens that were fused to the parts of g3p that were missing from the non-infectious phage particle (reviewed by Spada et al. 1997). These particles depend for their infectivity on an interaction between the ligand-binding protein and their respective ligand.

The g3-minus helper phages R408-d3 and M13ΔD3 mentioned above, lack in their genome a bacterial ORI and a selection marker. The absence of a selection marker in the g3-minus genomes has a significant effect on the production scale of helper phages, because it results in an overgrowth of bacteria that do not contain the helper phage genome. It is known that bacteria grow slower when infected with the helper phage or virus. Therefore, bacteria that lack the phage genome quickly overgrow the other bacteria that do contain the genome. Another effect of the lack of an ORI or a selection marker is that g3-minus phage genomes cannot be kept in dividing bacteria during the production and expansion of phage display libraries. This is a very important negative feature because overgrowth of bacteria that lost the phage genome or that did never receive one, appear to have a growth advantage over bacteria that do contain the phage genome. In addition, of course, such "empty" bacteria are not capable of producing any phage and, as a result, the phage display vectors including fusion protein fragments in such lacking-bacteria helper phages are lost permanently.

As mentioned, the g3p's are thought to be essential for the assembly of stable M13-like phages and, because of their crucial role in infection, g3p's should be provided otherwise when g3-minus helper phages are to be generated. There is a prejudice in the art against making phage display libraries that lack g3p's because phages lacking g3p's are not stable. Rakonjac et al. (1997) constructed a VCSM13 g3-minus helper phage in parallel to a R408 g3-minus helper phage and used helper plasmids, with either the psp or the lac promoter upstream of a full length g3 sequence, to substitute g3 during helper phage synthesis (Model et al. 1997). However, the art teaches that the lac promoter has the disadvantage that it cannot be shut off completely, not even in the presence of high concentrations of glucose (3–5%) in the medium (Rakonjac and Model, 1998). An additional problem that is well known in the art is that even very low levels of g3p in *E. coli* can block infection of M13-like phages. Moreover, it has been shown that co-encapsidation of plasmids, together with the phage genome, can occur (Russel and Model, 1989; Krebber et al. 1995; Rakonjac et al. 1997). If co-encapsidation occurs with the lac-driven helper plasmid, it will compete with the lac-driven vectors used in the phage display, resulting in the efficient production of infectious phage particles that will not contain the g3p-X fusion product. Together, the art thus teaches that the lac promoter is not the best candidate promoter in the helper plasmid system. The psp promoter has the advantage of being relatively silent in *E. coli* until infection (Rakonjac et al. 1997). Upon M13-class phage infection, the psp promoter becomes activated and now the helper plasmid will produce g3 proteins. However, the disadvantage of this promoter is that the level of RNA production cannot be regulated with external factors, but has to be regulated by either mutating (and changing the activity of) the promotor, changing the ribosomal binding site (RBS) or other elements that influence the promotor activity. Calculating the ideal level of promotor activity in a specific *E. coli* strain can be time consuming and needs to be optimized for each *E. coli* strain separately. The art also teaches that the psp promotor system is not very attractive for large-scale helper phage production due to the inflexibility of *E. coli* strains, the time consuming optimization and the significant low level of helper phage production.

One other significant problematic feature of all helper phage systems described is the occurrence of unwanted recombination events between the helper genome and the (helper-) plasmids. The problem that confronts investigators in the art is the fact that the g3 DNA sequences in the helper phages are homologous to the g3 sequences in the phage display vector and/or the helper phage plasmid. In many cases, this results in recombination between the two DNA strains and, therefore, loss of functionality of the library as a whole.

It is an object of the present invention to deal with problems and drawbacks known from the art as described above, concerning the generation of phage particles and helper phages, the use of helper phages in the production of phage display libraries, and the problems and drawbacks known for the identification of relevant binding molecules using such libraries.

DISCLOSURE OF THE INVENTION

The current invention comprises methods and means that substantially lack the above outlined drawbacks and that are characterized in providing novel phage particles, such as chimaeric phages, novel helper phages, libraries comprising the chimaeric phages and methods and means to produce the chimaeric phages and the helper phages.

The invention provides a chimaeric phage having a coat comprising a mixture of proteins. The mixture comprises a fusion protein where a proteinaceous molecule is fused to a functional form of a phage coat protein. The mixture further comprises a mutant form of the phage coat protein, where the mutant form is characterized in that a phage comprising no wild type phage coat protein from which the mutant form is derived, having a coat comprising the mutant form and no copies of the functional form, is less infectious than a phage comprising no wild type phage coat protein from which the mutant form is derived, having a coat comprising the mutant form and at least one copy of the functional form. In another embodiment of the invention, the mutant form is characterized in that a phage comprising no wild type phage coat protein from which the mutant form is derived, carrying the mutant form and no copies of the fusion protein, is less infectious than a phage comprising no wild type phage coat protein from which the mutant form is derived and carrying, in addition to the mutant form, at least one copy of the fusion protein. Preferably, the mutant form is characterized in that a phage comprising no wild type phage coat protein from which the mutant form is derived, carrying the mutant form and no copies of the fusion protein or the functional form, is non-infectious. More preferably, the mutant form is further characterized in that a phage, having a coat comprising the mutant form in the presence or absence of copies of the functional form, is stable. "Stable" as used herein means that the part of g3p that is still present in the mutant form (and that is also present in the functional form) ensures features, such as DNA binding and rigidness of the phage, but does not contribute to infectiousness of the phage as do the domains in the functional form that are not present in the mutant form. The invention also provides an infectious phage containing at least one copy of a mutant form of a phage coat protein, where the mutant form has lost the ability to mediate infection of a natural host by the infectious phage.

In a preferred embodiment, the phage coat protein is the g3 protein (g3p) present in the coat of phages such as M13 and R408, and the mutant form comprises a mutation in the D1 and/or the D2 region of g3p. In a preferred aspect of the invention, the chimaeric phage or the infectious phage is part of a phage collection such as a phage display library. In a more preferred aspect of the invention, such a phage collection consists essentially of chimaeric phages or infectious phages provided by the invention. Also preferred are chimaeric phages or infectious phages according to the invention that comprise antibodies or fragments thereof as part of the fusion protein.

In another embodiment, the invention provides a method for producing a phage particle comprising the steps of providing a host cell with a first nucleic acid encoding a fusion protein. The fusion protein is comprised of a proteinaceous molecule fused to a functional form of a phage coat protein, providing the host cell with a second nucleic acid encoding a mutant form of the phage coat protein. The mutant form is characterized in that a phage comprising no wild type phage coat protein from which the mutant form is derived and having a coat comprising the mutant form and no copies of the functional form, is less infectious than a phage comprising no wild type phage coat protein from which the mutant form is derived and having a coat comprising at least one copy of the functional form. The host cell comprises an additional nucleic acid sequence encoding at least all other proteins or functional equivalents thereof that are essential for the assembly of the phage particle in the host cell and culturing the host cell to allow assembly of the phage particle. Preferably, the method for producing a phage particle is applied for producing the chimaeric phage or the infectious phage. More preferably, the method is applied for producing a phage particle, such as a chimaeric phage or an infectious phage provided by the invention, that comprises nucleic acid encoding the mutant form under the control of a controllable promoter such as the AraC/BAD promoter.

In another embodiment, the invention provides a helper phage comprising nucleic acid encoding phage proteins or functional equivalents thereof that are essential for the assembly of the helper phage. The nucleic acid further encodes a mutant form of a phage coat protein. The mutant form is characterized in that a phage comprising no wild type phage coat protein from which the mutant form is derived, having a coat comprising the mutant form and no copies of a functional form of the phage coat protein, is less infectious than a phage comprising no wild type phage coat protein from which the mutant form is derived and having a coat comprising at least one copy of the functional form. The functional form is characterized in that it renders a phage particle carrying the functional form in its coat infectious, and where the helper phage does not comprise nucleic acid encoding the functional form.

In yet another embodiment, the invention provides a method for producing a helper phage comprising the steps of providing a host cell with a first nucleic acid encoding a functional form of a phage coat protein and providing the host cell with a second nucleic acid encoding a mutant form of the phage coat protein. The mutant form is characterized in that a phage comprising no wild type phage coat protein from which the mutant form is derived and having a coat comprising the mutant form, is less infectious than a phage comprising no wild type phage coat protein from which the mutant form is derived and having a coat comprising at least one copy of the functional form. The host cell comprises an additional nucleic acid sequence encoding at least all other proteins or functional equivalents thereof that are essential for the assembly of the helper phage in the host cell and culturing the host cell to allow assembly of the helper phage.

In another aspect, the invention provides methods and means for producing a phage particle, such as a chimaeric phage, an infectious phage or a helper phage. Separate nucleic acids, encoding either (1) a functional form of the phage coat protein alone or fused to a proteinaceous molecule or (2) a mutant form of the phage coat protein, each comprise codons in the overlapping regions between the protein encoding parts and essentially do not render a homologous recombination event between the separate nucleic acids. In a preferred aspect, separate nucleic acids each comprise non-interfering origins of replication and unique selection markers.

In another embodiment, the invention provides a method for the enrichment of a first binding pair member in a repertoire of first binding pair members selected from the group consisting of an antibody, an antibody fragment, a single chain Fv fragment, a Fab fragment, a variable region, a CDR region, an immunoglobulin or a functional part thereof. The first binding pair member is specific for a second binding pair member and comprises the steps of contacting a phage collection, comprising chimaeric or infectious phages according to the invention, with material comprising the second binding pair member under conditions allowing specific binding, removing non-specific binders, and recovering specific binders, the specific binders comprising the first binding pair member. The material may comprise second binding pair members such as purified proteins, recombinant proteins and/or proteins present on cells. In a preferred embodiment, the invention provides a method for the enrichment of a first binding pair member that further comprises the steps of recovering from a phage a DNA sequence encoding the first specific binding pair member, subcloning the DNA sequence in a suitable expression vector, expressing the DNA sequence in a suitable host, and culturing the suitable host under conditions whereby the first specific binding pair member is produced. A suitable expression vector may be a plasmid vector comprising an active promoter that regulates the expression of the first specific binding pair member in suitable hosts like eukaryotic cells, such as yeast cells or mammalian cells.

In another aspect, the invention provides a nucleic acid molecule comprising a sequence encoding a mutant form of a phage coat protein. The mutant form is characterized in that a phage comprising no wild type phage coat protein from which the mutant form is derived, having a coat comprising the mutant form and no functional form of the phage coat protein, is less infectious than a phage comprising no wild type phage coat protein from which the mutant form is derived, having a coat comprising the mutant form and at least one copy of the functional form of the phage coat protein. The functional form is characterized in that it renders a phage carrying the functional form in its coat infectious. The nucleic acid molecule may further comprise all relevant nucleic acid encoding proteins that are required for assembly of a phage in a host cell.

BRIEF DESCRIPTION OF THE FIGURES

FIG. 8. Codon usage adaptation in the g3 gene and the D3 domain to prevent homologous recombination during helper phage production and during phage display library amplification. The left panel shows the obtained one-letter coded amino acids and the right panel shows the optimal codons.

DETAILED DESCRIPTION OF THE INVENTION

Figure 1:
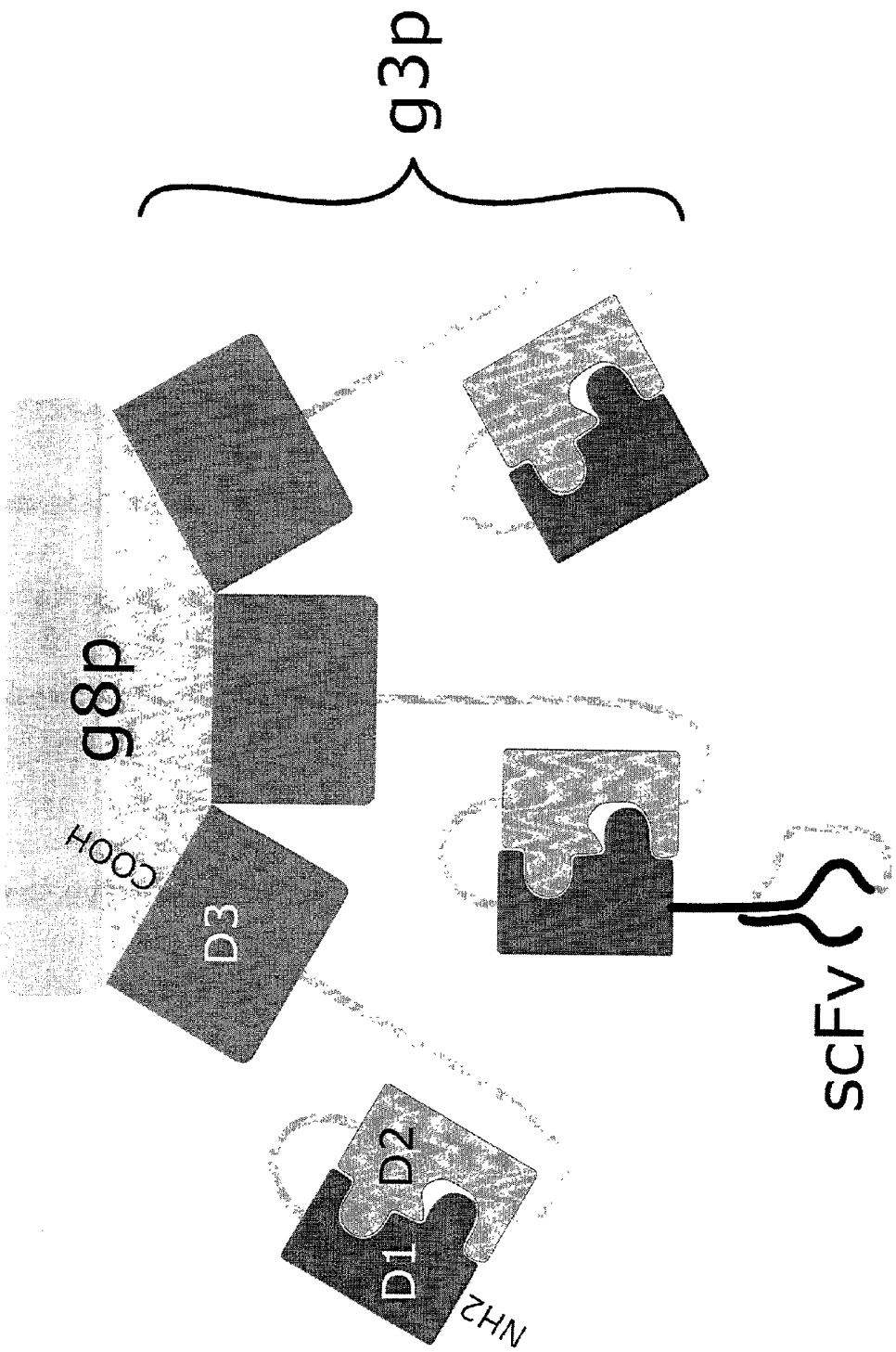
FIG. 1. Schematic representation of the g3 protein (g3p) present in the coat of M13 phages. The D3 domain of g3p is attached to the single stranded DNA inside the particle via the g8 protein (g8p), while the D1 and D2 domains interact with each other outside the particle and can be used for fusion with, for example, scFv.

The invention provides a chimaeric phage having a coat comprising a mixture of proteins. The mixture comprises a fusion protein where a proteinaceous molecule is fused to a functional form of a phage coat protein. The mixture further comprises a mutant form of the phage coat protein. The mutant form is characterized in that a phage comprising no wild type phage coat protein from which the mutant form is derived, having a coat comprising a mutant form of the phage coat protein and no copy or copies of the functional form of the phage coat protein, is less infectious than a phage comprising no wild type phage coat protein from which the mutant form is derived and having a coat comprising at least one functional form of the phage coat protein. "Functional form" as used herein refers to a phage coat protein that contributes significantly to the infectiousness of the particle to which it is attached. The phage coat protein itself is not infectious, but the functional form renders the phage particle to which it is attached infectious. Besides the contribution to infectivity of the phage particle, the phage coat protein also sustains other functions such as stabilization of the phage particle. A mutant form of a phage coat protein according to the invention may render the phage particle less infectious or non-infectious but should still sustain other functions of the phage coat protein such as stabilization of the phage. A phage that comprises no wild type phage coat protein from which the mutant form is derived and comprises no functional forms of the phage coat protein, but does contain only mutant forms of the phage coat protein, is less infectious than a phage that comprises no wild type phage coat protein from which the mutant form is derived and comprises one or more functional forms of the phage coat protein next to the mutant forms of the phage coat protein in its coat. "Less infectious" as used herein may also mean non-infectious. Although a chimaeric phage of the invention comprises at least one copy of the mutant form of the phage coat protein in its coat, the chimaeric phage has infectious capability because it also comprises at least one functional form of the phage coat protein in its coat. A "functional form of a phage coat protein" as used herein also means a part, derivative and/or an analogue thereof that still harbors functionality in rendering the phage infectious to which it is attached. "Mutant form of a phage coat protein" as used herein also means a part, a derivative and/or an analogue of the mutant form, where the mutant form is characterized in that a phage comprising no wild type phage coat protein from which the mutant form is derived and having a coat comprising only mutant forms of the phage coat protein or parts, derivatives and/or analogues thereof, is less- or non-infectious as compared to a phage comprising no wild type phage coat protein from which the mutant form is derived and having a coat comprising at least one functional form of the phage coat protein.

In a preferred embodiment, the phage coat protein is the g3 protein (g3p) that, in a wild type or functional form, renders a phage to which it is attached, infectious. In another preferred embodiment, the mutant form of the phage coat protein comprises an alteration in the g3 protein consisting of a mutation in either the D1 region, the D2 region, or both. A "mutation" as used herein means one or multiple point mutations, stretches of mutations, deletions, substitutions, replacements and/or swapping of parts. In a more preferred embodiment, the alteration in the g3 protein is a deletion of substantially all of the D1 and/or the D2 region. "Alteration" as used herein may also mean a substitution of the deleted g3 protein part by a protein or a peptide not contributing to the infectivity of the helper phage, the chimaeric phage, the infectious phage or the phage particle.

In an even more preferred embodiment of the invention, a chimaeric phage or an infectious phage comprises a nucleic acid encoding a fusion protein, where a proteinaceous molecule is fused to a functional form of the phage coat protein and where the chimaeric phage of the invention comprises a M13, M13K07, VCSM13 or a R408 strain or a mutant, derivative or analogue strain derived from either one of these strains. A proteinaceous molecule according to the invention is fused to the functional form of the phage coat protein and comprises a protein such as a ligand-binding moiety or an immunoglobulin (such as an antibody). A proteinaceous molecule may also mean a peptide such as a random stretch of amino acids or a non-random stretch of amino acids such as an antibody fragment or derivatives thereof (Fab fragment, a single chain Fv fragment (scFv), a variable region or a CDR region). A proteinaceous molecule can also mean first specific binding pair member or can mean fusions between different kinds of (fragments of) proteins and/or fusions between (fragments of) proteins and (random and non-random) peptides such as antibody-recognized tags.

Figure 2:
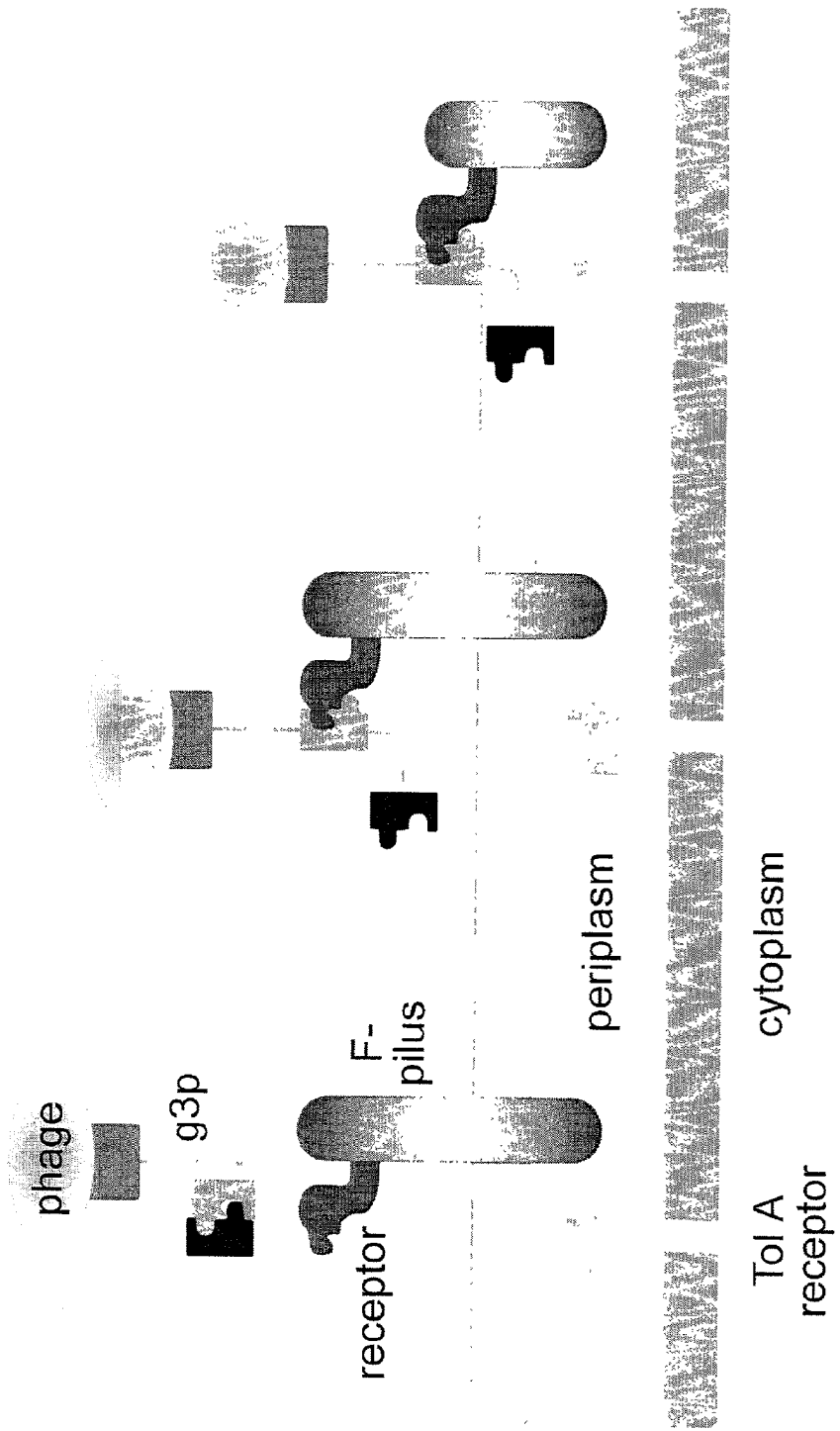
FIG. 2. Schematic representation of the interaction between the D2 domain of g3p with the F-pilus on the surface of *E. coli*, with a subsequent interaction of the D1 domain with other components of the bacterial surface.
Figure 3:
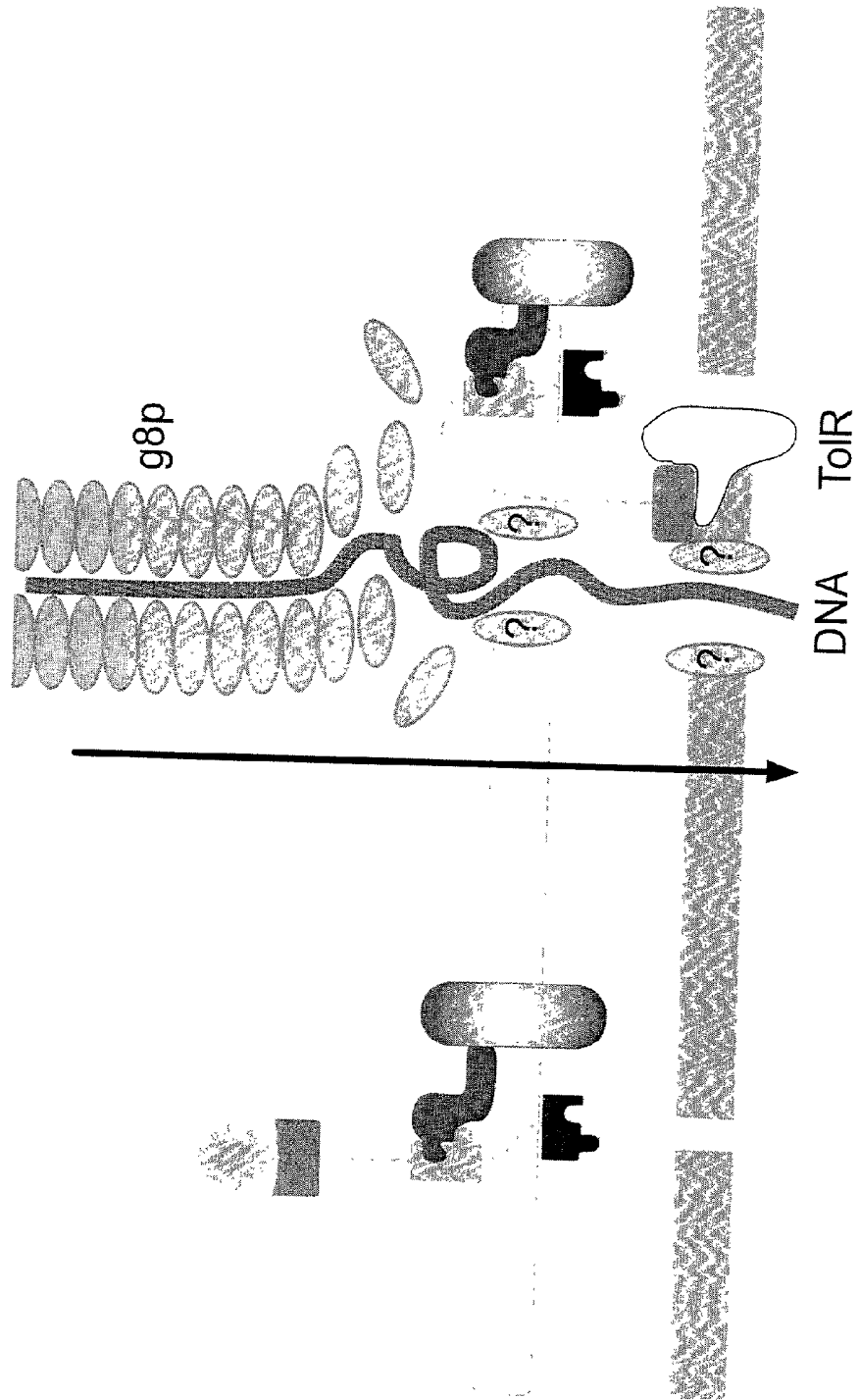
FIG. 3. Schematic representation of the interaction of the D2 domain of g3p with the F-pilus (left) and the D1 domain of g3p with the TolA receptor (see FIG. 2) and the subsequent entry (right) of the phage genome into the cytoplasm of the bacterium.
Figure 4:
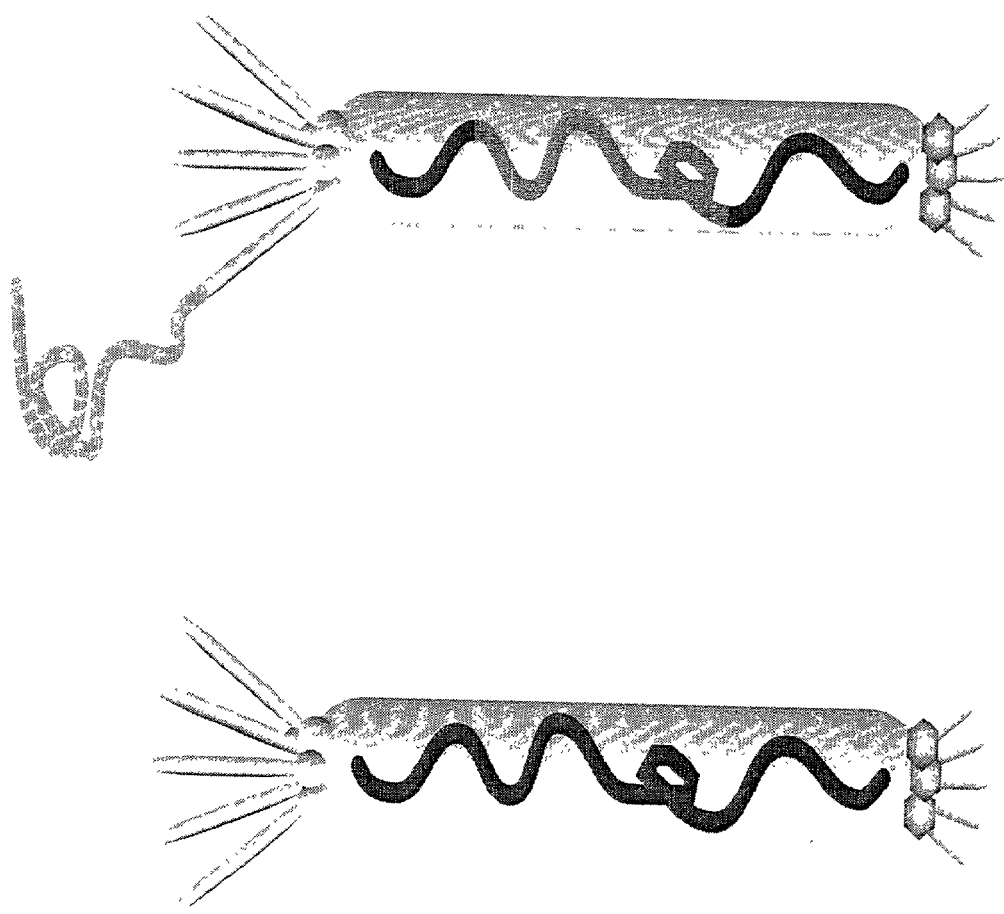
FIG. 4. Schematic representation of a wild type phage expressing five g3p's on its infectious end (left) and a recombinant phage expressing four wild type g3p's and one g3p-X fusion protein on its infectious end (right). The recombinant phage also harbors the genetic information of the fusion protein present on the surface.

The g3 protein (g3p) of M13 phages and M13-derivatives comprises three functional domains, D1, D2 and D3, linked by two glycin-rich linkers. Considering that functionality of a D3 domain of the protein is required for assembly of stable phages, a less- or non-infectious mutant of the phage coat protein preferably comprises a D3 region of the g3p, or comprises a functional part, derivative and/or analogue of the D3 region. The D3 domain is thought to bind to DNA inside the viral particle. Loss of the D3 domain functionally results in rare phage-like particles that are very long and very fragile (Pratt et al. 1969; Crissman and Smith, 1984; Rakonjac and Model, 1998). The D1 and D2 domains are thought to interact with each other until the phage binds to the bacteria. Studies in which a protease cleavage site was introduced between D1 and D2 showed that after cleavage, the phage particle became non-infectious (Kristensen and Winter, 1998). Functional analysis of g3p showed that of the g3p N-terminal regions, the D1 domain is essential for infection. Loss of this domain results in phages that cannot infect bacteria (Lubkowski et al. 1998; Nelson et al. 1981; Deng et al. 1999; Riechmann and Holliger, 1997; Holliger and Riechmann, 1997). It has been shown that the D2 domain interacts with the D1 domain of g3p on the phage (FIG. 1). Due to competition of proteins located on the F-pilus (on F$^+$ bacteria) that have higher affinity for D2 than for D1, the D1 and D2 domains of the g3p dissociate from each other. The binding of D2 to the F-pilus results in a process that leads to retraction of the F-pilus towards the *E. coli* cell membrane. Due to this process, the phage particle comes in close contact with the bacterial membrane. The dissociated D1 domain can now interact with bacterial proteins, such as the TolA receptor, leading to the introduction of the phage DNA into the *E. coli* cell (Lubkowski et al. 1999). The fact that removal of the D2 domain does not prevent infection but enables phages to infect *E. coli* lacking F-pili (Riechmann and Holliger, 1997; Deng et al. 1999), shows that the presence of the D2 domain increases specificity and that D2 has an important role in preventing F-pili independent infections. The binding of D1 to the specific receptors on the surface of the *E. coli* cell (a feature that is not F$^+$-specific) is represented in FIG. 2. This process triggers the injection of the viral genome into the bacterium (as depicted in FIG. 3). Although loss of the D2 domain results in the formation of phage particles that can infect *E. coli* in a somewhat reduced specific manner, it appears that the level of infections from such a population of phages is significantly reduced. A chimaeric phage of the invention relies significantly for infection on the functional form of the phage coat protein and on the presence of part(s) of the phage coat protein that contribute to the infectivity of the phage. The mutant form of the phage coat protein is mutated in the part(s) of the phage coat protein that render the phage infectious. The mutation is exemplified in, but not limited to, deletions, residue- or fragment substitutions, swaps and/or replacements by other protein fragments rendering it less infectious. The protein fragments may or may not be related to phage coat proteins or fragments thereof, and are essentially not capable of inducing infection of the phage particle into a host cell.

In another embodiment, the invention provides a phage collection comprising a chimaeric phage or an infectious phage. Phages of the present invention are particularly useful for the generation of phage display libraries. Therefore, in a more preferred embodiment, the phage collection is a phage display library. In an even more preferred embodiment, the phage collection consists essentially of chimaeric phages or of infectious phages of the invention. A proteinaceous molecule, such as (random or not random) stretches of amino acids, peptides, protein parts or even entire proteins, can be fused to the phage coat proteins and can form a first specific binding pair member. This fusion is typically done at the terminal ends of the coat protein and typically does not affect the function of the phage coat protein. Moreover, it also often does not interfere with the function of the added moiety. Thus, it is possible to generate libraries that, for instance, can be used to locate and clone specific binding molecules. Such libraries can comprise peptides or larger molecules. Preferably, the larger molecules comprise a protein such as an antibody or a functional part, derivative and/or analogue thereof, such as full length heavy and/or light chains from an immunoglobulin molecule, or fragments of immunoglobulins such as Fab fragments, single chain Fv (scFv) fragments, CDR regions, sole variable regions and/or combinations of the above.

In another aspect, the invention provides a method for making a phage particle which comprises the steps of providing a host cell with a first nucleic acid encoding a fusion protein. The fusion protein comprises a proteinaceous molecule fused to a functional form of a phage coat protein or to a functional part, derivative and/or analogue of the phage coat protein, providing the host cell with a second nucleic acid encoding a mutant form of the phage coat protein. The mutant form is characterized as described above, where less infectious may also mean non-infectious, and culturing the cell allows assembly of the phage. The host cell, otherwise or additionally, comprises nucleic acid encoding at least all essential proteins or functional equivalents of the essential proteins for the assembly of the phage particle. In a preferred embodiment, the invention provides a method where the nucleic acid encoding at least all other proteins or functional equivalents thereof that are essential for the assembly of the phage particle in the host cell is comprised by a helper phage. The helper phage is used to deliver the nucleic acid to the host cell. In a more preferred embodiment, the nucleic acid that is delivered by the helper phage also comprises the second nucleic acid encoding the mutant form of the phage coat protein. In an even more preferred embodiment, the first and second nucleic acids are separate nucleic acids that each may comprise separate unique selection markers to ensure that the host cell comprises at least one copy of each separate nucleic acid, each comprising separate unique origins of replication to ensure no interferences during replication. In another aspect of the invention, the number of possible homologous recombination events between overlapping stretches of nucleic acid sequences between the separate nucleic acids is reduced due to the use of different codons within each nucleic acid.

Using a method of the invention, it is possible to generate phage particles that comprise at least two variants derived from the same coat protein. The relative number of the variants can vary. Typically, one wants to influence the relative amount of the various variants in the phage coat. To that end, it is preferred that expression of the fusion protein and/or expression of the mutant form of the phage coat protein is regulatable. Preferably, this is achieved by regulating the expression of the gene encoding the phage coat protein at a transcriptional level. Thus, preferably, expression of the fusion protein and/or the mutant form of the phage coat protein is under the control of a promoter that is well controlled. Particularly advantageous is the AraC/BAD promoter. The AraC/BAD promoter is preferred because it is a promoter that is controlled in a very tight manner. This promoter is, for all practical purposes, silent in the presence of glucose and only slightly leaky in the absence of glucose. In addition, the activity of the promoter can be regulated very tightly by the addition of arabinose to the medium. The concentration of arabinose used determines the level of protein expressed in *E. Coli* cells. Therefore, optimal regulation of phage coat protein is accomplished by using this AraC/BAD promoter and by altering the culturing conditions of the host cell. The use of a promoter that is dependent on arabinose, such as the AraC/BAD promoter, instead of IPTG, such as lac-operon, prevents problems that will occur due to co-encapsidation of the helper plasmid in viral particles during helper phage synthesis. As described above, it has been shown that co-encapsidation of plasmids together with the phage genome do occur (Russel and Model, 1989; Krebber et al. 1995; Rakonjac et al. 1997). If co-encapsidation occurs with a lac-driven helper plasmid, it will compete with the lac-driven vectors generally used for the phage display, resulting in the efficient production of infectious phage particles that will not contain the g3p-X fusion product. This problem does not occur when the AraC/BAD promoter is used.

A method of the invention for the production of a phage particle is preferably used to produce a chimaeric phage according to the invention. The host can be provided with nucleic acid encoding a phage protein in any suitable way. Preferably, however, the host is provided with a helper phage according to the invention. A helper phage according to the invention comprises nucleic acid encoding other phage proteins or functional equivalents thereof that are essential for the assembly of the helper phage. The nucleic acid further encodes a mutant form of a phage coat protein. The mutant form is characterized in that a phage comprising no wild type phage coat protein from which the mutant form is derived, having a coat comprising mutant forms of the phage coat protein and no functional forms of the phage coat protein, is less infectious than a phage comprising no wild type phage coat protein from which the mutant form is derived and having a coat comprising at least one functional form of the phage coat protein and where the helper phage does not comprise nucleic acid encoding a functional form of the phage coat protein. Other phage proteins means other than the functional form of the phage coat protein and the mutant form of the phage coat protein. Nucleic acid encoding the latter may be provided to the host cell in an alternative fashion. However, the helper phage may further comprise nucleic acid encoding the functional form of the phage coat protein or the mutant form, or both. Preferably, the helper phage does not comprise nucleic acid encoding the fusion protein. In this way, the helper phage is uniform and may be used to produce phages that preferentially comprise nucleic acid encoding the fusion protein in the absence of nucleic acid encoding any other required helper phage protein. Thus, preferably, the fusion protein and the mutant form of the phage coat protein are encoded by separate nucleic acids. Preferably, each of the separate nucleic acids comprises a unique selection marker. Preferably, the separate nucleic acids comprise non-interfering origins of replication, where the origins of replication do not compete with one another, resulting in bacterial cells that tolerate the separate nucleic acids for the generation of new phage particles.

The art teaches that it has been very difficult to generate helper phage batches, where the helper phages harbor nucleic acid that encodes for all essential proteins required for assembly of a phage particle in a bacterial host cell and where the nucleic acid lacks a gene encoding for g3p. Subsequently, the art teaches that it is difficult to produce phage libraries using such helper phages. Several difficulties are known in the art that hamper a proper generation of such helper phage batches. The present invention provides methods, means and a good combination of features, such as the use of specific origins of replication, selection markers and codons in overlapping stretches of DNA, that enable the production of phage batches containing high titres of useful helper phages, that can subsequently be applied for the generation of chimaeric or infectious phages according to the invention. Therefore, in one embodiment, the invention provides methods and means for the production of helper phages that carry functional forms and/or wild type forms of a phage coat protein in their coat, but that, nevertheless, lack nucleic acid encoding for the functional form and/or the wild type form of the phage coat protein. The invention provides a method for producing a helper phage comprising the steps of: providing a host cell with a first nucleic acid encoding a functional form of a phage coat protein and providing the host cell with a second nucleic acid encoding a mutant form of the phage coat protein. The mutant form is characterized in that a phage comprising no wild type phage coat protein from which the mutant form is derived, having a coat comprising mutant forms of the phage coat protein and no copies of the functional form, is less infectious than a phage comprising no wild type phage coat protein from which the mutant form is derived, having a coat comprising at least one functional form of the phage coat protein, and culturing the host cell to allow assembly of the helper phage. The host cell additionally comprises nucleic acid encoding at least all other proteins or functional equivalents thereof that are essential for the assembly of the helper phage in the host cell. Preferably, the method does not comprise the incorporation of a wild type form of the phage coat protein in the helper phage. Preferably, the phage coat protein is the g3 protein present in the coat of most, if not all, bacteriophages. Preferably, other proteins are encoded by the second nucleic acid. The expression of the mutant form of the phage coat protein and/or the expression of the functional form is regulated by altering the culturing conditions of the host cell and is preferably under the control of a controllable promoter such as the AraC/BAD promoter as described above.

A phage coat protein is said to be contributing significantly to the infectiousness of a phage when it allows, upon incorporation in a phage, the phage to infect a bacterial host in a manner comparable to a wild type version of the phage coat protein, in kind, not necessarily in amount. As used herein, the terms "less-infectious" or "non-infectious" refer to a phage carrying no functional or wild type forms of a phage coat protein, preferably g3p, and that exhibit a significant diminished infectious capability as compared to the wild type phage (particle) as determinable in, for instance, plaque assays well known to persons skilled in the art. As used herein, the terms "less-infectious" and "non-infectious" may also refer to a decrease in host cell specificity. In general, a non-infectious phage is unable to enter a bacterial cell as outlined for wild type phages in FIGS. 2 and 3, whereas a less infectious phage is capable of doing so with less efficiency. Preferably, a phage having mutant forms infects the host cell with an efficiency which is less than 50% compared to a phage carrying at least a functional form, more preferably less than 10%, still more preferably less than 1%, under conditions which are otherwise comparable.

In embodiments where the phage coat protein comprises a g3p, the mutant form preferably comprises at least a structural part, derivative and/or analogue of the D3 region. The structural part, derivative and/or analogue comprise at least the functionality of g3p to allow assembly of stable phage particles.

A "derivative of a protein" as used herein comprises the same activity in kind, not necessarily in amount, as the protein the derivative is derived from. When the protein is a functional form of a phage coat protein, the derivative comprises the same functionality in kind, not necessarily in amount. When the protein is a mutant form of a phage coat protein, the derivative is also a mutant form of the phage coat protein. When the protein is a mutant form of a phage coat protein that renders a phage carrying only mutant forms of the phage coat protein less infectious, the derivative also is a phage coat protein that renders a phage carrying only derivatives and/or mutant forms of the phage coat protein less infectious. Typical derivatives are proteins comprising one or more conservative amino acid substitutions. However, derivatives may also comprise insertions and/or deletions. Furthermore, derivatives may also comprise swaps of amino acids or sequences of amino acids within the same protein or between two or more related and/or unrelated proteins. An "analogue of a protein" as used herein comprises the same activity in kind, not necessarily in amount, as the protein the analogue is analogous to. When the protein is a functional form of a phage coat protein, the analogue comprises the same functionality in kind, not necessarily in amount.

Prior to the invention, it has been difficult to generate sufficient numbers of helper phages that lack a functional g3 gene or a part, derivative and/or analogue thereof in their genome, but that, nevertheless, are infectious for one round of infection through E. coli cells. The present invention succeeds in generating such helper phages efficiently. Such helper phages carry functional forms and/or wild type g3 proteins (g3p's) on their surface but, nevertheless, lack nucleic acid encoding the functional form and/or the wild type g3 protein. The invention further provides methods and means to generate libraries comprising chimaeric phages with the help of such helper phages. Preferably, phage display libraries are generated. More preferably, libraries display a large variety of single chain Fv (scFv) fragments. Using the means and methods of the invention, phage libraries can be generated that contain a significantly higher number of infectious phages as compared to the number of non- or less-infectious phages than were described and are present in the art. At the same time, the helper phages used to produce such libraries become (through an infection round in E. coli cells) essentially non-infectious because the g3 gene is not present in an infectivity-contributing form in the phages. Thus, after infection of a bacterial host, the phages cannot spread to other bacterial cells except, of course, through division of the already infected host into daughter cells. Such libraries are, therefore, also provided by the invention. The generated libraries are particularly useful for panning experiments because the titers of phages per milliliter are significantly higher than was used in the art until the present invention. Moreover, libraries of the invention display less a-specific stickiness. Thus, the libraries display less false positives than libraries in the art. Moreover, after one round of panning, only phages that display a functional form on their surface (preferably fused to a proteinaceous molecule) can be amplified in E. coli cells, while phages that do not carry any functional forms of the phage coat protein but only carry mutant forms of the phage coat protein, are essentially non-infectious and cannot be amplified on E. coli cells. Therefore, the number of remaining phages that are used for a second round of panning is significantly decreased. As a result of using the chimaeric phages of the invention present in the libraries provided by the present invention, the number of panning rounds is decreased and the number of relevant binders is obtained in a much more sufficient manner as was possible before the present invention.

In another aspect, the invention provides nucleic acids and helper phages comprising the nucleic acids that comprise genomic DNA sequences in which at least the domains of g3p that are responsible and contributing to infection are functionally removed. The invention also provides helper phage genomic DNA's in which the leader and at least the D3 domain are unaffected and fused together. The nucleic acids are preferably based on VCSM13 and M13K07 genomic sequences. Due to a lack of a functional D1 domain, phage particles produced by the nucleic acids are essentially non-infectious. "Essentially" in this context means that no spread, or at least significantly less spread, of the phages to other bacterial cells than the production bacterium occurs through g3p provided infectious features. This absence of spread to other bacterial cells is due to the absence of a functional form of g3p. If, during production, a source for wild type form or functional form of g3p is provided, produced phages can infect a bacterium. However, if the bacterium produces phages as a result of the infection, then a resulting phage particle is not capable of infecting another bacterium unless, again, a source for infectious g3p is provided during production. A chimaeric phage or an infectious phage of the invention preferably comprises a part of g3p that ensures the generation of a stable phage particle after one round of infection in E. coli cells. To this end, the helper phage preferably comprises a nucleic acid encoding a mutant form of g3p. Preferably, the mutant form comprises D3 or a functional part, derivative and/or analogue thereof.

A phage display library can, for instance, be generated by providing a collection of bacteria with a library of nucleic acids encoding g3p fused to a range of different proteinaceous molecules and infecting the bacteria with helper phages of the invention. In a particularly preferred embodiment, a library of phage display particles that is produced with these helper phages contains phages that do not carry any infectious parts of g3p on their surface and phages that carry one or two full length g3p-X fusions, next to non-infectious or less-infectious parts of g3p deletion proteins. Phages in these library mixtures that do not express g3p-X fusion proteins can no longer infect bacteria since they were generated in the absence of infectious g3p parts that are not fused to X (X comprises a proteinaceous molecule or a fusion partner of interest, such as immunoglobulins or fragments of immunoglobulins such as Fab fragments or scFv fragments).

In one aspect, the invention provides helper phages that combine the presence of a selection marker with the presence of a bacterial origin of replication (ORI) to overcome the described problems in the production of g3-minus helper phages and, subsequently, for the generation of phage display libraries. The presence of such a combination ensures the production of large amounts of helper phages and/or helper genomes. g3-minus helper phages with an ORI and a resistance marker can be made from the g3-minus helper phages VCSM13 and M13K07. These helper phages, unlike M13 or R408, do contain a kanamycine resistance gene from the Tn903 transposon and a P15A ORI that are both inserted in the intergenic region of the phage genome. Another aspect of the invention is the fact that because of this resistance gene and the presence of this particular ORI, these helper phages can grow easily in large quantities, while empty, or no plasmid- or no genome-containing bacteria are removed under the selection pressure, and that no interferences occur between ORI's from the phage genome and the helper plasmid or between ORI's from the phage genome and the display library plasmids, when both nucleic acids are present in the same bacterial host cell. VCSM13 and M13K07 contain the P15A ORI. To prevent the disappearance of the helper genome or the helper vector, the ORI's should not cause any interferences and, therefore, P15A derived ORI's are not used in the vector. For the vector applied for the production of helper phages, the ColE1 ORI was chosen to ensure that the copy number of helper plasmids can only reach low or moderate levels and to minimize the possibility of recombination, growth delay, high g3p expression levels and non-specific incorporation of the helper vector in the virus particle. Besides the features and effects mentioned above, it is also important that the helper vector for the generation of helper phages does not carry an F1 ORI to prevent the incorporation of the helper vector in the phage particle instead of the viral genome.

The invention also provides vectors enabling a regulated expression of the mutant form and/or the functional form of g3p by the use of a regulatable promoter as stated above and that, furthermore, contain a resistance gene that is different from the kanamycine resistance gene present in the helper genome. This complementary resistance is here provided by the beta-lactamase (ampicillin) gene since its product is relatively stable and ensures complete killing of bacteria that does not express the gene product.

The pBAD/gIII vector (Invitrogen) can be used as a backbone vector for the production of helper vectors of the invention. Preferably, further features of this basic helper vector are that regions of sequence homology are minimized which significantly decreases the possibility of homologous recombination.

The invention further provides the use of TOP10 and LMG host cell bacterial cells (Invitrogen) for the production of helper phages that contain a g3-minus genome but are, nevertheless, infectious due to the g3p present on the phages because it was delivered by the helper vector. The genotype of these bacteria ensures that they can transport arabinose into the cell but that they cannot metabolize it (genotype: araABCD- and araEFGH+). In addition, the TOP10 bacteria are recA and endA deficient which diminishes the chance of recombination and mutation. Furthermore, the TOP10 bacteria are F-, which makes them resistant to phages that might contaminate phage batches of interest.

The present invention provides further a partially deleted g3 gene that is still present in the helper phage genome to provide stable but essentially non-infectious helper phages that harbor infectious g3p's on their coat. The invention describes this partially deleted g3 gene that is made synthetically by using synthetic primers in such a way that the functionally deleted g3 gene encodes the same protein on an amino acid level as compared to the other part of the g3 gene that is present in the same bacterium, but the codons that are used do not lead to homologous recombination events. Because the leader sequences in the different settings are very different, there is no need to change these regions in the helper genome, phage display vector (with the scFv encoding genes) or helper vector. In principle, it does not matter whether the g3 gene in the helper genome, in the phage display vector or helper vector has been changed as long as the two overlapping (in amino acid content) and previously homologous g3 parts that are introduced into one E. coli cell do not match.

The present invention describes the use of codon changes in the g3 gene for the production of helper phages that are infectious due to g3p's encoded by the helper vectors but that lack a wild type or at least an infectious g3 gene in their genome and for the production of chimaeric phages according to the invention. The use of codon changes ensures a diminished chance for homologous recombination effects that might occur during the process of helper phage generation. The invention preferably provides the use of codon changes in the g3 gene or parts thereof for the generation of phage display libraries in which the helper phage genome that is brought into an E. coli cell, together with nucleic acids encoding for g3p-X fusion proteins, is not homologous to the g3 gene present in the DNA encoding for the g3p-X fusion protein. These codon changes ensure that the chance for homologous recombination events in the generation of phage display libraries is significantly decreased through which the quality of these libraries and uses thereof are significantly improved.

EXPERIMENTAL PROCEDURES

Primers

The following primers (Genset, France) were used in the generation of the different vectors and helper phage genomic constructs. Most restriction enzymes hardly, or fail to, digest DNA if their corresponding palindrome is near the end of the DNA. Therefore, a stretch of 8 nucleotides was added to the 5' end of all of these primers in which this stretch is an A/T rich non-hybridizing 8-mer.

```
D3 primers
D3 BamHI Forward
5'-GGATCC TCTGGTTCCGGTGATTTGATTATG-3'
SEQ ID NO:1
D3 BamHI Backward
5'-GGATCC AGCGGAGTGAGAATAGAAAGGAAC-3'
SEQ ID NO:2 g3-minus primers
g3 minus HindIII Forward
5'-AAGCTT CTGCGTAATAAGGAGTCTTAATCATGC-3'
SEQ ID NO:3
g3 minus HindIII Backward
5'-AAGCTT GTTGAAAATCTCCAAAAAAAAGGC-3'
SEQ ID NO:4 g3 ORF primers
g3 ORF NcoI Forward
5'-CCATGG CTGAAACTGTTGAAAGTTGTTTAGC-3'
SEQ ID NO:5
g3 ORF XbaI Backward
5'-TCTAGA TTAAGACTCCTTACGCAGTATG-3'
SEQ ID NO:6
```

PCR Reactions and Product Isolation

All PCR reactions were, as a standard (except for the elongation time of the DNA synthesis cycle step), performed using the following 50 µl hot start PCR scheme and the AmpliTaq PCR kit from Perkin Elmer: 1 µl 10 mM dNTP (Roche Diagnostics), 4 µl 25 mM $MgCl_2$, 5 µl 10× PCR buffer supplied with the kit, 5 µl 2.5 µM Forward primer, 5 µl 2.5 µM Backward primer, 0.3 µl 5 units/µl AmpliTaq, 10–50 ng template, sterile bi-distilled water. All components were kept on ice until placing in the pre-heated PCR block. The standard program was as follows: 12 cycles of 25 seconds 94° C., 52° C. annealing for 25 sec, 72° C. polymerization ending with one cycle of 72° C. for seven minutes followed by an indefinitive storage at 4° C. The time of polymerization for new helper genome synthesis was 12 min, and for g3 amplification and for AraC gene and AraC/BAD promoter amplification this was set at 90 seconds.

All PCR products were separated on 0.5%–1% TBE agarose gels containing 100 ng/ml ethidium bromide. After imaging, the desired fragments were cut out using sterile disposable chirurgical knives and isolated with Qiagen's gel purification kit according to the guided protocol.

Ligation Reactions

All ligation reactions were performed in the following reaction mixtures:

50 ng vector or helper genome
25 ng insert
4 µl 5× ligation buffer (Gibco BRL)
1 µl T4-ligase (Gibco-BRL, 200 units/µl)
sterile bi-distilled water to 20 µl The mixtures were incubated overnight at 6–10° C. Then, 30 µl sterile water, 5 µl K-acetate 3M pH 4.8 acidic acid adjusted (KAc), 1 µl glycogen 10 mg/ml and 50 µl isopropanol were added and mixed thoroughly. After 15 minutes of precipitation, the tubes were centrifuged at maximum speed at 4° C. for ten minutes. The pellet was washed once with 1 ml 70% ethanol and after drying, dissolved in 10 µl sterile water. Half of this volume was used for electroporation, together with 50 µl competent cells.

Sequencing

Sequencing of the clones was performed according to the instruction guide sent along with the Rhodamine BigDye terminator kit with a few adaptations. The reaction volume was scaled down to 12.5 µl. 4 il Qiagen mini prep purified DNA (8%) was used as template. All clones were sequenced in order to verify the correctness of the products.

Electroporation

All bacterial strains, except those that were used for the helper phage production, were acquired from manufacturers as electroporation-competent cells with the highest competence available and transformed according to the manufacturers' protocol using 0.1 cm cuvettes (BioRad). The production of helper phages, however, is dependent on TOP10 or LMG cells (Stratagene) containing the helper plasmid (pBAD/gIII-g3). These cells were made competent and stored at −80° C. until use as follows: One colony of the bacteria was used to inoculate in 10 ml 2× TY with ampicillin (100 µg/ml) and for LMG also with tetracycline (10 µg/ml) and cultured by vigorously shaking at 30° C. overnight. Next, the cultures were spun down at 3000 rpm for five minutes. The pellet was resuspended in 500 ml fresh 2× YT including the antibiotics and cultured until OD 0.5 in a 2 1 Erlenmeyer flask on a shaking platform at 37° C. These cells were allowed to cool on ice-water for 45 minutes and centrifuged in pre-cooled buckets and rotor at 3000 rpm at 4° C. for 25 minutes in a Sorvall centrifuge using a GLA-3000 rotor. The supernatant was discarded and the cells were slowly and carefully resuspended in 100 ml ice-cold 10% glycerol. The centrifugation and glycerol steps were repeated twice. The final pellet was taken up very carefully in 5 ml 10% ice-cold glycerol and aliquoted in pre-cooled eppendorf tubes. Next, these tubes were immersed in a mixture of ethanol and dry ice for five minutes to ensure very quick freezing of the cells. The tubes containing the electrocompetent cells were stored at −80° C. until use.

Phage Production

The desired F⁺ E. coli strain is inoculated in 2× YT medium containing the required antibiotics and cultured at 37° C. at 220 rpm until OD 0.2. The (helper-) phage is added to the culture and incubated for 30–45 minutes at 37° C. in a non-shaking waterbath. Then, kanamycine (50 µg/ml) is added to the cells and the cells are further incubated at 220 rpm at 37° C. for 30–45 minutes. Subsequently, this solution is spun at 3500 rpm at room temperature for 15 minutes. The supernatant is removed carefully and the pellet is brought to the desired volume of 2× YT medium containing all required antibiotics. Cells are cultured overnight at 30° C. for a phage display library and at 37° C. for regular (helper-) phages on a shaking platform.

Titer Determination

One colony of Xl1blue (Stratagene) is inoculated in 5 ml 2× YT containing 10 µg tetracycline per ml (YT-T) in a 50 ml tube (Flacon) and cultured at 37° C. at 220 rpm overnight. 200 µl of this culture is added to 5 ml YT-T and cultured until OD 0.2. Then, the phage stock is diluted in YT and a dilution series as required is made to determine the number of plaque forming units. For each dilution step, 100 µl of the O.D. 0.2 XL1Blue culture is taken and added to 100 µl of the phages. This mixture is incubated for 25 minutes at 37° C. in a waterbath (not shaking). The 200 µl of bacterial cells is pipetted onto a 2× YT-broth plate containing the required antibiotics. The suspension is spread using a sterile glass rod. After drying the plates, they are inverted and transferred into a 37° C. incubator. After overnight culture, the number of colonies are counted. Each colony indicates the presence of 1 infective phage particle in the original phage solution. The number of infectious particles per ml of the analyzed stock is calculated. The phage particles are ELISA tested according to the protocol supplied with anti-M13 and anti-M13-HRP conjugate (Pharmacia).

Isolation of DNA from Phages

An overnight phage culture is grown as described above. If a large scale isolation of DNA was required, the BioRad Plasmid Maxi Prep kit was used according to the manufacturers' instructions, except for the elution step which is done with 10 mM Tris pH 8.5 at 65° C. for ten minutes. Small or medium scale isolations were performed using Qiagen's mini-prep kit according to the instructions supplied with the kit except for the elution step. The elution step here was performed at 65° C. for ten minutes.

PEG Precipitation

The medium containing bacteria and phages is collected in 450 ml buckets. The mixture is spun in a pre-cooled Sorvall centrifuge using a GSA-3000 rotor at 8000 rpm for 20 minutes. Then, 90 ml 20% PEG/2.5 M NaCl is pipetted into clean 450 ml buckets. 360 ml of the supernatant of the centrifuged medium containing the phages is brought into the PEG-containing buckets and mixed well. The mixture is set on ice water for two hours or overnight in the fridge. The precipitate is pelleted by centrifugation in a pre-cooled Sorvall centrifuge at 8000 rpm for 20 minutes. The supernatant is decanted and the buckets are left to drip out for five minutes in order to remove as much Precipitation buffer as possible. Subsequently, 32 ml PBS/1% bovine serum albumin (BSA) is added to the 450 ml buckets containing the pelleted phages and buckets are rotated on a bottle roller for 15 minutes. The solution is transferred to a SS-34 compatible centrifuge tube and spun in a pre-cooled Sorvall centrifuge containing a SS-34 rotor (or equivalent equipment) for 25 minutes at 13,000 rpm. This step removes all kinds of debris and small bacteria. In the meantime, the plunger is removed from a 50 ml syringe and attached to a 0.45 µM filter (Whatmann). The centrifuged supernatant is transferred into the syringe and pushed through the filter. This step removes all small bacteria and other cells. 8 ml 20% PEG/2.5 M NaCl is added and mixed well. The tubes are set on ice for one hour. The high speed centrifugation step is repeated as described above. The supernatant is decanted and the tube is let to drip out on a paper towel for five minutes. The phage pellet is dissolved in 5 ml PBS/1% BSA. Then, 5 ml 100% glycerol is added to the phage solution and mixed well. Phages are stored at −20° C. Typically, the solution contains approximately 2 to $5 \times 10^{13}$ infectious phage particles per ml.

EXAMPLES

To illustrate the invention, the following examples are provided, but not intended to limit the scope of the invention.

Example 1

Cloning of the pBAD/gIII-g3 helper vector.

Figure 5:
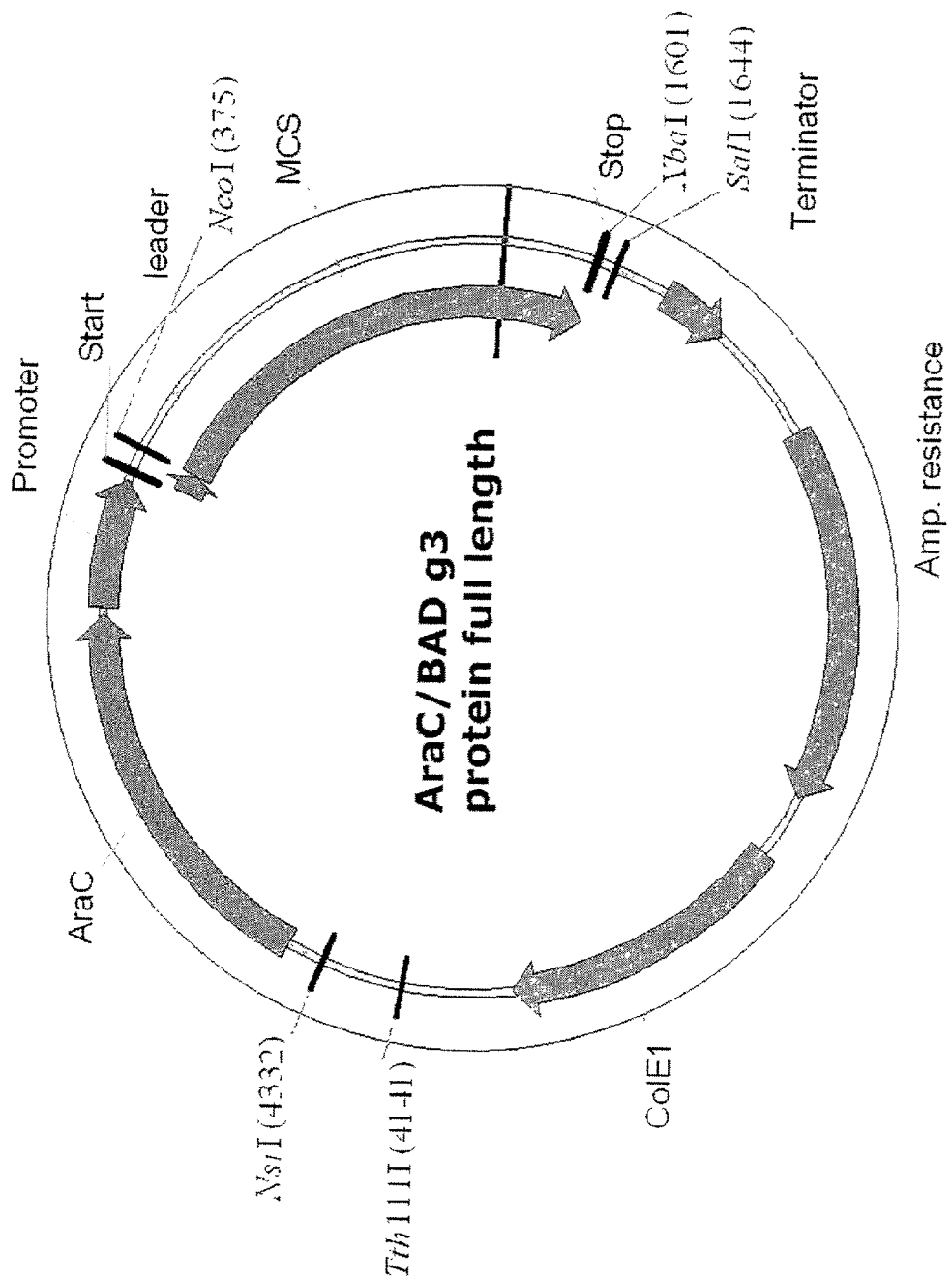
FIG. 5. Schematic representation of the pBAD/gIII-g3 helper vector harboring the full length g3 gene under the control of the AraC/BAD promoter and further harboring an ampicillin resistance and a ColE1 origin of replication (ORI).

The full Open Reading Frame (ORF) of the g3 gene was generated by using M13KO7 (Gibco-BRL) DNA as a template in a standard PCR reaction together with g3 ORF NcoI Forward and g3 ORF XbaI Backward primers. The purified PCR product and the pBAD/gIII vector were both digested with NcoI (NEB) and XbaI (Roche Diagnostics) simultaneously in buffer H (Roche Diagnostics) for four hours at 37° C. After ligation, isolation, and electroporation in TOP10 (Stratagene) and LMG (Stratagene) cells, two correct clones were selected by sequencing and grown on a large scale followed by the isolation of the DNA. The DNA was reprecipitated with 70% ethanol and in the presence of KAc and the pellet was washed twice with 70% ethanol. After drying, the DNA was solved in sterile bi-distilled water and stored at −20° C. until use. The resulting plasmid is depicted in FIG. 5. This helper vector contains the full-sized g3 gene under the control of the AraC/BAD promoter, ampicillin resistance gene and a ColE1 ORI as its most important features.

Example 2

Cloning of the g3 minus helper phage genome g3⁻-HP.

Figure 6A:
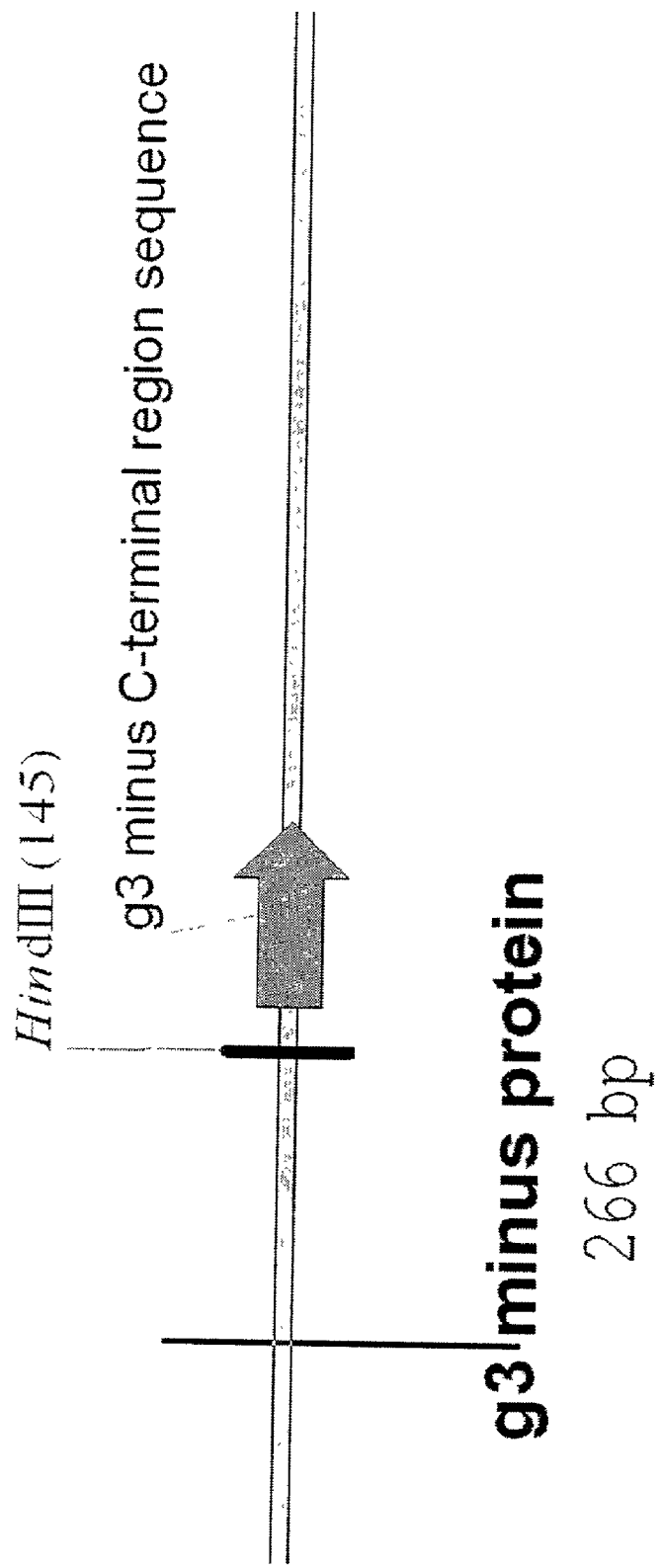
FIG. 6.(A) Schematic representation of the helper phage genome deleted for the open reading frame (ORF) of the g3 gene. The arrow indicates the 3' end of the gene that remained after cloning procedures. (B) SEQ ID NO:7, which represents the sequence of the part of the helper phage genome that surrounds the position of the g3 deletion depicted in (A).

The use of g3 minus HindIII Forward and g3 minus HindIII Backward primers and M13KO7 and VCSM 13 as templates in a standard PCR reaction resulted in the formation of a PCR product that contained HindIII sites at both ends of the DNA. After separation, gel isolation and purification, digestion with HindIII (Roche Diagnostics) and re-purification of the DNA, the product was self-ligated under standard ligation conditions and electroporated into XL1Blue cells (Stratagene). The transformed cells were resuspended in 5 ml 2TY medium and cultured shaking at 37° C. for one hour. Kanamycin was added to an end-concentration of 50 µg/ml and the cells were allowed to grow at the same conditions for another five hours. The culture was centrifuged at 3000 rpm for 15 minutes and the supernatant passed through a 0.22 µM filter to remove bacteria. At the same time, a culture of exponentially growing XL-1 Blue bacteria was prepared. Fractions of the filtrate (50–1000 µl) containing phage particles were added to 5 ml of XL-1 Blue bacteria and incubated at 37° C. for 30 minutes without shaking. The culture was centrifuged again, the supernatant discarded and the cells were plated on 2× YT-K-T plates and transferred into an incubator at 37° C. for overnight growth. Eight correct clones that lack the g3 ORF (checked through the BamHI site) and include the introduced HindIII site were isolated and used for g3-less helper phage production in the presence of the pBAD/gIII-g3 helper plasmid. Only two clones that were able to form phages in the presence of the helper plasmid were kept. From these clones, a large quantity of DNA was isolated and stored for further experiments. The obtained g3-minus helper phage genome is depicted schematically in FIG. 6A, while the correct sequence of this construct surrounding the HindIII and BsrI sites is depicted in FIG. 6B as SEQ ID NO:7.

Example 3

Cloning of a helper phage genome with a partially deleted g3 gene.

Figure 7A:
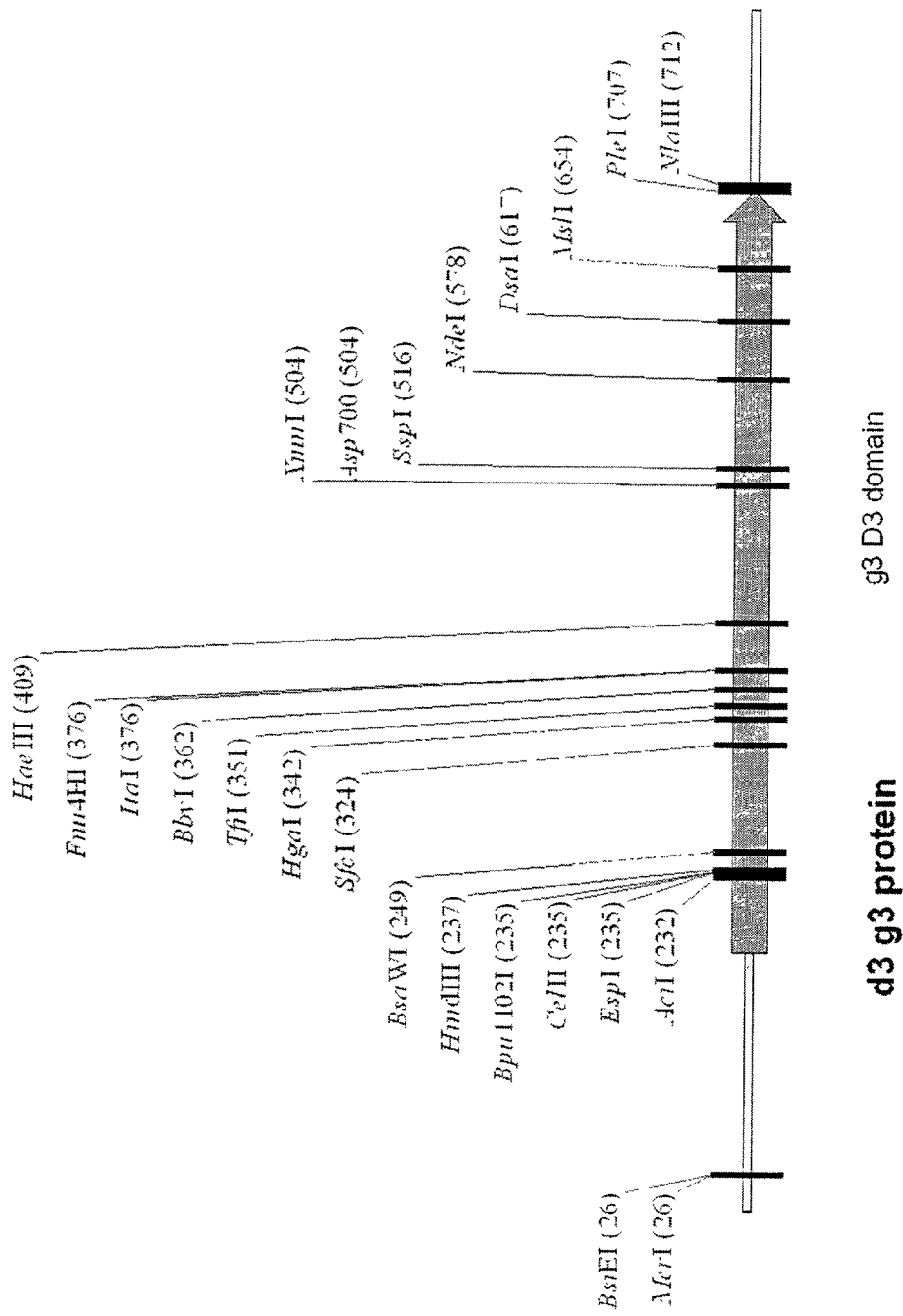
FIG. 7.(A) Schematic representation of the helper phage genome deleted for the part of the g3 gene that contributes to the infectivity of the phage. The arrow indicates the D3 part of the g3 gene that encodes the carboxy-terminal part of the g3 protein enabling the generation of stable, but essentially non-infectious helper phages. (B) SEQ ID NO:8, which represents the sequence of the nucleic acid that is shown in (A).

The construction of helper phage genome that express only the D3 part of the g3 gene was comparable to the above described g3-less helper phages with the exception that the primers used were D3 BamHI Forward and D3 BamHI Backward primers in order to generate the new genome. All other procedures were the same as for the g3-less procedure, except for the use of BamHI instead of HindIII. In the end, the DNA of two correct clones was kept and stored at −20° C. The final construct of the helper phage genome that still expresses the part of the g3 gene that does not contribute to the infectiousness of the phage particle is depicted in FIG. 7A, while the sequence surrounding the PCR product insert in the genome is depicted in FIG. 7B as SEQ ID NO:8.

Example 4

Production of infectious helper phages that do not carry a gene encoding the wild type g3p.

The procedures for generating g3-less and generating partially deleted g3 (or D3 expressing) helper phages are identical. Frozen competent TOP10 or LMG cells that contain the pBAD/gIII-g3 helper plasmid were electroporated using 100 ng helper phage DNA. After recovery, the cells were transferred into 4× 250 ml 2× YT-K-A medium supplemented with 0.05% arabinose (Sigma). Phages were produced during overnight culture at 37° C. and vigorous shaking. The next day the phages were purified and stored according to the standard procedures of precipitation and storage that were described supra. The number of infectious particles and the number of phages were determined by titration and ELISA procedures that were also described supra. For g3-less helper phages, approximately $5\times10^{11}$ infectious particles were synthesized, while for D3, approximately $5\times10^{13}$ infectious phages were formed using these procedures.

Example 5

Amplification and harvesting of phage display libraries containing infectious phages carrying g3p-scFv fusions and non-infectious helper phages, using g3 minus and partially g3 deleted helper phages.

A frozen library was inoculated as follows. In general, approximately 5–10 µg concentrated stocks were inoculated in 25 ml 2× YT containing the required antibiotics and 5% glucose and grown at 37° C. with vigorous shaking. At OD 0.3–0.4 (after about 2–3 hours), a 500–1000 fold excess of helper phage was added. The medium containing the helper phages and bacteria was incubated in a water bath at 37° C. without shaking for 25 minutes. Removal of dead cells and excess of phage particles was realized after a centrifugation step at 3000 rpm for 15 minutes. The pellet was resuspended in 250 ml 2× YT with antibiotics but without glucose and grown at 30° C. with good aeration overnight. The next day, the formed phages were isolated and stored using the standard PEG/NaCl procedure.

Example 6

Codon usage in g3 and the partially deleted g3 gene (D3) to prevent homologous recombination during helper phage production and library amplification.

In order to prevent possible recombinations between a genomic nucleic acid encoding the helper phage g3 protein region (or a part thereof, such as the D3 domain) and other nucleic acids (like the phage display vector and the AraC/BAD helper vector), a series of helper phages are designed that contain changed codons within the g3p region. Newly translated g3p's are identical to the wild type g3 protein or protein part (D3). Due to these changes, g3-ORF coding DNA domains cannot, or barely, recombine with the phage display vectors or the AraC/BAD-g3 helper vector. The codons that are used to generate non-homologous g3 genes are depicted in FIG. 8 and are optimal for the *E. coli* transcription machinery.

PCR generation of helper phage genomes (VCSM13, M13K07, D3, g3-minus or AraC/BAD) with g3-leader backward and g3 end forward primers with NotI restriction sites ensure the generation of PCR products containing all helper phage components and genes, except for the g3 ORF.

New g3 regions are constructed with overlapping primers and are inserted in helper phages. The PCR-generated g3p or parts thereof are digested with NotI and ligated in the NotI digested PCR generated helper phage genome. After transformation and selection of correct helper genomes (with a new g3 gene), helper phages are grown as described.

Example 7

Selection of thyroglobulin-interacting phages using a library amplified with helper phages comprising only the D3 part of g3p in their genome.

In order to validate the D3 helper phages in standard phage selections, a selection was performed using an antibody phage display library that was amplified using the D3 helper phages as described above. Procedures that were used were essentially as described by De Kruif et al. (1995a). Briefly, thyroglobulin was coated to a plastic tube. The tube was blocked in PBS containing 2% milk (MPBS) whereafter the antibody phage display library, also blocked in MPBS, was added to the tube. The phages were allowed to bind for two hours, whereafter non-binding phages were removed by washing the tube in PBS containing 0.1% Tween-20 as described by De Kruif et al. (1995a). The binding phages were eluted in 50 mM Glycin/HCl pH 2.2 (ten minutes at RT) and used to infect freshly grown XL-1 Blue bacteria. The bacteria were plated on 2TY agar plates containing the appropriate antibiotics and glucose, incubated overnight at 37° C. and used to prepare an enriched phage display library; phage D3 was again used as helper phage. The procedure was repeated once, whereafter individual *E. coli* colonies were used to prepare monoclonal phage antibodies. These monoclonal phage antibodies were tested in ELISA for their ability to bind specifically to the thyroglobulin antigen. Results show that after two rounds of selection, 25/46 colonies show positive binding to thyroglobulin. Previously we found that by using a general VCS-M13 as a helper phage, at least three rounds of selection were required to obtain specific binders in this selection format.

Example 8

Selection of phages interacting with myeloma cells using a library amplified with helper phages comprising only the D3 part of g3p in their genome.

In order to validate the D3 helper phages in selections on intact cells, a selection was performed using an antibody phage display library that was amplified using the D3 helper phage. Procedures that were used were essentially as described by De Kruif et al. (1995a and 1995b). Briefly, myeloma cells (AML, CD33+, CD34+) were obtained from the blood of a patient undergoing treatment at the Utrecht University Hospital (The Netherlands). 0.5 ml phage library was added to 3 ml RPMI medium containing 10% FCS (RPMIS) and incubated on ice for 15 minutes. The myeloma cells were added and the cell suspension was rotated at 4° C. for two hours. The cells were washed five times in 50 ml ice-cold RPMIS whereafter the binding phages were eluted (in 50 mM Glycin/HCl pH 2.2 for ten minutes at RT) and used to infect freshly grown XL-1 Blue bacteria. The bacteria were plated on 2TY agar plates containing the appropriate antibiotics and glucose, incubated overnight at 37° C. and used to prepare an enriched phage display library. Again, the D3 expressing helper phages were used as helper. The procedure was repeated once, whereafter individual *E. coli* colonies were used to prepare monoclonal phage antibodies. These monoclonal phage antibodies were tested in FACS procedures for their ability to bind myeloma cells. Results show that 23 out of 41 clones tested bound specifically to epitopes expressed on the myeloma cells. Generally, three or more rounds of selection are required to obtain similar numbers of binding phages using identical procedures, with the exception of using VCS-M13 helper phages instead of the helper phages described by the invention.

REFERENCES

Balint R F and Larrick J W (1993) Antibody engineering by parsimonious mutagenesis. Gene 137:109

Barbas C F, Hu D, Dunlop N, Sawyer L, Cababa D, Hendry R M, Nara P L, Burton D R (1994) In vitro evolution of a neutralizing human antibody to human immunodeficiency virus type 1 to enhance affinity and broaden strain cross-reactivity. Proc Natl Acad Sci USA. 91:3809

Bass S H, Greene R and Wells J A (1990) Hormone phage: An enrichment method for variant proteins with altered binding properties. Proteins 8:309–314

Beekwilder J, Rakonjac J, Jongsma M, Bosch D (1999) A phagemid vector using the *E. coli* phage shock promoter facilitates phage display of toxic proteins. Gene 288: 23–31

Berek C, and Milstein C (1987) Mutation drift and repertoire shift in the maturation of the immune response. Immunol Rev 96:23

Burton D R and Barbas C F (1994) Human antibodies from combinatorial libraries. Adv Immunol 57:191

Crissman J W and Smith G P (1984) Gene-III protein of filamentous phage: evidence for a carboxyl-terminal domain with a role in morphogenesis. Virology 132: 445–455

Cwirla S E, Peters E A, Barrett R E and Dower W J (1990) Peptides of phage: A vast library of peptides for identifying ligands. Proc Natl Acad Sci USA 87:6378–638

De Kruif J, Boel E and Logtenberg T (1995a) Selection and application of human single chain Fv antibody fragments from a semi-synthetic phage antibody display library with designed CDR3 regions. J Mol Biol 248: 97–105

De Kruif J, Terstappen L, Boel E and Logtenberg T (1995b) Rapid selection of cell subpopulation-specific human monoclonal antibodies from a synthetic phage antibody library. Proc Natl Acad Sci USA 92:3938–3942

Deng L W, Malik P, Perham R N (1999) Interaction of the globular domains of pIII protein of filamentous bacteriophage fd with the F-pilus of *Escherichia coli*. Virology 253:271–277

Devlin J J, Panganiban L C and Devlin P E (1990) Random peptide libraries: A source of specific protein binding molecules. Science 249:404–406

Dueòas M, Borrebaeck C A (1995) Novel helper phage design: intergenic region affects the assembly of bacteriophage and the size of antibody libraries. FEMS microbiology letters 125:317–322

Felici F, Luzzago A and Cortese R (1993) Mimicking of discontinuous epitopes by phage displayed proteins. II. Selection of clones recognized by a protective monoclonal antibody against the *Bordetella pertussis* toxin from phage peptide libraries. Gene 128:21–27

Hawkins R E, Russel S J, Winter G (1992) Selection of phage antibodies by binding affinity: mimicking affinity maturation. J Mol Biol 226:889

Holliger P, Riechmann L (1997) A conserved infection pathway for filamentous bacteriophage is suggested by the structure of the membrane penetration domain of the minor coat protein g3p from phage fd. Structure 5:265–275

Hoogenboom H R (1994) Designing and optimizing library selection strategies for generating high-affinity antibodies. Trends in Biotechnol. 15:62

Krebber C, Spada S, Desplancq D, Pluckthun A (1995) Co-selection of cognate antibody-antigen pairs by selectively-infective phage. FEBS Lett. 377:227–31

Kristensen P, Winter G (1998) Proteolytic selection for protein folding using filamentous bacteriophage. Folding and Design 3:321–328

Low N M, Holliger P H, Winter G (1996) Mimicking somatic hypermutation: affinity maturation of antibodies displayed on bacteriophage using a bacterial mutator strain. J Mol Biol 260:359

Lubkowski J, Hennecke F, Pluckthun A, Wlodawer A (1998) The structural basis of phage display elucidated by the crystal structure of the N-terminal domains of g3p. Nat Struct Biol 5:140–147

Lubkowski J, Hennecke F, Pluckthun A, Wlodawer A (1999) Filamentous phage infection: crystal structure of g3p in complex with its coreceptor, the C-terminal domain of TolA. Structure 7:711–722

Luzzago A, Felici F, Tramontano A, Pessi A and Cortese R (1993) Mimicking of discontinuous epitopes by phage displayed proteins. I. Epitope mapping of human H ferritin using a phage display library of constrained peptides. Gene 128:51–57

Lopez J and Webster R E (1983) Morphogenesis of filamentous bacteriophage f1: orientation of extrusion and production of polyphage. Virology 127:177–193

Model P, Jovanovic G, Dworkin J. (1997) The *Escherichia coli* phage shock protein (psp) operon. Mol Microbiol 24:255–261

Nelson F K, Friedman S M and Smith G P (1981) Filamentous phage DNA cloning vectors: A noninfective mutant with a nonpolar deletion in gene III. Virology 108: 338–350

Pratt D, Tzagoloff H and Beaudoin J (1969) Conditional lethal mutants of the small filamentous coliphage. H. Two genes for coat proteins. Virology 39:42–53

Rakonjac J, Jovanovic G, Model P. (1997) Filamentous phage infection-mediated gene expression: construction and propagation of the gIII deletion mutant helper phage R408D3. Gene 198:99–103

Rakonjac J, Model P. (1998) Roles of pIII in filamentous phage assembly. J Mol Biol 282:25–41

Riechmann L, Holliger P (1997) The C-terminal domain of TolA is the coreceptor for filamentous phage infection of *E. coli*. Cell 90:351–360

Russel M, Model P (1989) Genetic analysis of the filamentous bacteriophage packaging signal and of the proteins that interact with it. J Virol 63:3284–3295

Smith GP (1985) Filamentous fusion phage: Novel expression vectors that display cloned antigens on the surface of the virion. Science 228:1315–1317

Spada S, Krebber C and Pluckthun A (1997) Selectively infective phages (SIP). Biol Chem 378:445–456

Vaughan T J, Osbourn J K, Tempest P R (1998) Human antibodies by design. Nat Biotechnol 16:535

Winter G, Milstein C (1991) Man-made antibodies. Nature 349:293

Yang W-P, Green K, Pinz-Sweeney S, Briones A T, Burton D R, Barbas C F (1995) CDR walking mutagenesis for the affinity maturation of a potent human ant-HIV-1 antibody into the picomolar range. J Mol Biol 254:392

The invention claimed is:

1. A method of producing a chimaeric filamentous phage particle, the method comprising the steps of:
   a) providing a host cell with a first nucleic acid encoding a fusion protein, wherein the fusion protein comprises a proteinaceous molecule fused to a g3 phage coat protein capable of mediating infection of a host by the chimaeric filamentous phage particle;
   b) providing the host cell with a second nucleic acid encoding a mutant form of the g3 phage coat protein, wherein the mutant form comprises deletion of the D1 region, D2 region or both regions of the g3 coat protein, the second nucleic acid further encoding all other proteins that are essential for the assembly of a filamentous phage particle in the host cell; and
   c) culturing the host cell to allow assembly of the chimaeric filamentous phage particle, the chimaeric filamentous phage particle displaying a mixture of proteins on its surface, the mixture comprising the mutant form of the g3 phase coat protein and the fusion protein, wherein the fusion protein is attached to the chimaeric filamentous phage particle via the g3 phage coat protein capable of mediating infection of a host by the chimaeric filamentous phage particle.

2. The method of claim 1, wherein the second nucleic acid is provided by a helper phage to the host cell.

3. The method of claim 1, wherein the expression of the fusion protein, the mutant form of the g3 phage coat protein, or both is regulatable by altering the culturing conditions of the host cell.

4. The method of claim 1, wherein the expression of the fusion protein, the mutant form of the g3 phage coat protein, or both is under control of a regulatable promoter.

5. The method of claim 4, wherein the regulatable promoter comprises the AraC/BAD promoter.

6. The method of claim 1, wherein the first nucleic acid and the second nucleic acid each comprise a unique selection marker.

7. The method of claim 1, wherein the first nucleic acid and the second nucleic acid each comprise a unique origin of replication.

8. The method of claim 1, wherein the first nucleic acid and the second nucleic acid comprise codons that do not lead to homologous recombination between the first nucleic acid and the second nucleic acid.

9. The method of claim 1, wherein the proteinaceous molecule comprises a binding molecule.

10. The method of claim 9, wherein the binding molecule is an antibody, a Fab fragment, a single chain Fv fragment, a variable region, a CDR region, an immunoglobulin or a functional part thereof.

11. The method of claim 1, wherein the chimaeric filamentous phage particle comprises the first nucleic acid.

12. The method of claim 1, wherein the chimaeric filamentous phage particle lacks the second nucleic acid.

13. The method of claim 1, wherein the chimaeric filamentous phage particle is derived from a M13, M13K07, VCSM13 or a R408 strain.

14. A method of producing a chimaeric filamentous phage particle, the method comprising the steps of:
   a) providing a host cell with a first nucleic acid encoding a fusion protein, wherein the fusion protein comprises a proteinaceous molecule fused to a g3 phage coat protein capable of mediating infection of a host by the chimaeric filamentous phage particle;
   b) providing the host cell with a second nucleic acid encoding a mutant form of the g3 phage coat protein, wherein the mutant form comprises deletion of the D1 region, D2 region or both regions of the g3 phage coat protein, said host cell further comprising a nucleic acid encoding all other proteins that are essential for the assembly of a filamentous phage particle in the host cell; and c) culturing the host cell to allow assembly of the chimaeric filamentous phage particle, the chimaeric filamentous phase particle displaying a mixture of proteins on its surface, the mixture comprising the mutant form of the g3 phase coat protein and the fusion protein, wherein the fusion protein is attached to the chimaeric filamentous phage particle via the g3 phage coat protein capable of mediating infection of a host by the chimaeric filamentous phage particle.

* * * * *

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Primer D3 BamHI Forward

<400> SEQUENCE: 1
ggatcctctg gttccggtga tttgattatg                                    30

<210> SEQ ID NO 2
<211> LENGTH: 30
<212> TYPE: DNA
<213> ORGANISM: Artificial sequence
<220> FEATURE:
<223> OTHER INFORMATION: Primer D3 BamHI Backward

<400> SEQUENCE: 2
ggatccagcg gagtgagaat agaaaggaac                                    30
```

<210> SEQ ID NO 3
<211> LENGTH: 33
<212> TYPE: DNA
<213> ORGANISM: Artificial sequence
<220> FEATURE:
<223> OTHER INFORMATION: Primer g3 minus HindIII Forward

<400> SEQUENCE: 3
aagcttctgc gtaataagga gtcttaatca tgc                       33

<210> SEQ ID NO 4
<211> LENGTH: 31
<212> TYPE: DNA
<213> ORGANISM: Artificial sequence
<220> FEATURE:
<223> OTHER INFORMATION: Primer g3 minus HindIII Backward

<400> SEQUENCE: 4
aagcttgttg aaaatctcca aaaaaaagg c                          31

<210> SEQ ID NO 5
<211> LENGTH: 31
<212> TYPE: DNA
<213> ORGANISM: Artificial sequence
<220> FEATURE:
<223> OTHER INFORMATION: Primer g3 ORF NcoI Forward

<400> SEQUENCE: 5
ccatggctga aactgttgaa agttgtttag c                         31

<210> SEQ ID NO 6
<211> LENGTH: 31
<212> TYPE: DNA
<213> ORGANISM: Artificial sequence
<220> FEATURE:
<223> OTHER INFORMATION: Primer g3 ORF XbaI Backward

<400> SEQUENCE: 6
tctagattaa gactccttat tacgcagtat g                         31

<210> SEQ ID NO 7
<211> LENGTH: 266
<212> TYPE: DNA
<213> ORGANISM: Artificial sequence
<220> FEATURE:
<223> OTHER INFORMATION: Sequence of the part of the helper phage that
      surrounds the g3 deletion

<400> SEQUENCE: 7
ggttatgcgt gggcgatggt tgttgtcatt gtcggcgcaa ctatcggtat caagctgttt      60
aagaaattca cctcgaaagc aagctgataa accgatacaa ttaaaggctc cttttggagc     120
cttttttttt ggagattttc aacaagcttc tgcgtaataa ggagtcttaa tcatgccagt     180
tcttttgggt attccgttat tattgcgttt cctcggtttc cttctggtaa ctttgttcgg     240
ctatctgcta acttttctta aaaagg                                          266

<210> SEQ ID NO 8
<211> LENGTH: 832
<212> TYPE: DNA
<213> ORGANISM: Artificial sequence
<220> FEATURE:
<223> OTHER INFORMATION: Representation of the helper phage genome
      deleted for part of the g3 gene

<400> SEQUENCE: 8

-continued

```
ttgactccct gcaagcctca gcgaccgaat atatcggtta tgcgtgggcg atggttgttg          60
tcattgtcgg cgcaactatc ggtatcaagc tgtttaagaa attcacctcg aaagcaagct         120
gataaaccga tacaattaaa ggctccttt ggagccttt tttttggaga ttttcaacgt          180
gaaaaaatta ttattcgcaa ttcctttagt tgttcctttc tattctcact ccgctaagct        240
ttctggttcc ggtgattttg attatgaaaa tatggcaaac gctaataagg gggctatgac        300
cgaaaatgcc gatgaaaacg cgctacagtc tgacgctaaa ggcaaacttg attctgtcgc        360
tactgattac ggtgctgcta tcgacggttt cattggtgac gtttccggcc ttgctaatgg        420
taatggtgct actggtgatt ttgctggctc taattcccaa atggctcaag tcggtgacgg        480
tgataattca cctttaatga ataatttccg tcaatattta ccttccttc ctcaatcggt         540 tgaatgtcgc ccttttgtct ttcgcgctgg taaaccatat gaattttcta ttgattgtga        600
caaaataaac ttattccgtg gtgtctttgc gtttctttta tatgttgcca cctttatgta       660
tgtattttcg acgtttgcta acatactgcg taataaggag tcttaatcat gccagttctt       720
ttgggtattc cgttattatt gcgtttcctc ggtttccttc tggtaacttt gttcggctat       780
ctgctaactt ttcttaaaaa gggcttcggt aagatagcta ttgctatttc at                832
```